US008376973B2

(12) United States Patent
Flood

(10) Patent No.: US 8,376,973 B2
(45) Date of Patent: Feb. 19, 2013

(54) PATIENT KITS FOR RESUSCITATION OR CIRCULATORY SUPPORT SYSTEMS

(76) Inventor: Michael G. Flood, Pensacola, FL (US)

(*) Notice: Subject to any disclaimer, the term of this patent is extended or adjusted under 35 U.S.C. 154(b) by 137 days.

(21) Appl. No.: 12/890,675

(22) Filed: Sep. 26, 2010

(65) Prior Publication Data
US 2011/0098611 A1 Apr. 28, 2011

Related U.S. Application Data

(63) Continuation-in-part of application No. 12/493,005, filed on Jun. 26, 2009, now Pat. No. 8,277,399.

(51) Int. Cl.
A61H 31/00 (2006.01)
(52) U.S. Cl. .......................... 601/41; 601/149; 601/150
(58) Field of Classification Search .............. 601/41–44, 601/148–152; 602/13; 606/201, 202; 128/DIG. 20
See application file for complete search history.

(56) References Cited

U.S. PATENT DOCUMENTS

| 4,928,674 | A | 5/1990 | Halperin et al. | |
| 5,806,512 | A | 9/1998 | Abramov et al. | |
| 2003/0004445 | A1* | 1/2003 | Hall et al. | 601/41 |
| 2004/0030272 | A1 | 2/2004 | Kelly et al. | |

FOREIGN PATENT DOCUMENTS

| WO | WO2004004548 | 1/2004 |
| WO | WO2004004548 A2 | 1/2004 |
| WO | WO2010151278 A1 | 12/2010 |

OTHER PUBLICATIONS

International Search Report for PCT/US2011/047865, mailed Apr. 4, 2012.
Written Opinion of the International Searching Authority for PCT/US 2011/047865, mailed Apr. 4, 2012.
Invitation to Pay Additional Fees and, Where Applicable, Protest Fees re International Application No. PCT/US2011/047865.

* cited by examiner

Primary Examiner — Quang D Thanh
(74) Attorney, Agent, or Firm — Larry K. Roberts

(57) ABSTRACT

A patient interface kit for a system for providing cardiopulmonary resuscitation or circulatory support to a patient, the system including a control unit, the kit including an inflatable abdominal cuff adapted to extend over a patient's abdomen and including an elongated flexible strap, an inflatable bladder and a fastener system to secure the abdominal cuff in position for use on a patient; an inflatable chest cuff adapted to extend over a patient's chest and including an elongated flexible strap, an inflatable bladder and a fastener system to secure the chest cuff in position for use on a patient; a patient platform or backboard configured for disposition against the patient's back during use; and a cuff prepositioning system configured to secure the chest and abdomen compression cuffs to the patient platform in a ready position and to facilitate rapid deployment of the cuffs for use on the patient.

22 Claims, 17 Drawing Sheets

PATENT KITS FOR RESUSCITATION OR CIRCULATORY SUPPORT SYSTEMS

CROSS-REFERENCE TO RELATED APPLICATION

This application is a continuation-in-part of, and claims priority to, application Ser. No. 12/493,005, filed Jun. 26, 2009, now U.S. Pat. No. 8,277,399, the entire contents of which are incorporated herein by this reference.

BACKGROUND

U.S. Pat. No. 5,806,512 describes an apparatus to implement a resuscitation method.

BRIEF DESCRIPTION OF THE DRAWINGS

Features and advantages of the disclosure will readily be appreciated by persons skilled in the art from the following detailed description when read in conjunction with the drawing wherein.

DETAILED DESCRIPTION

Figure 1:
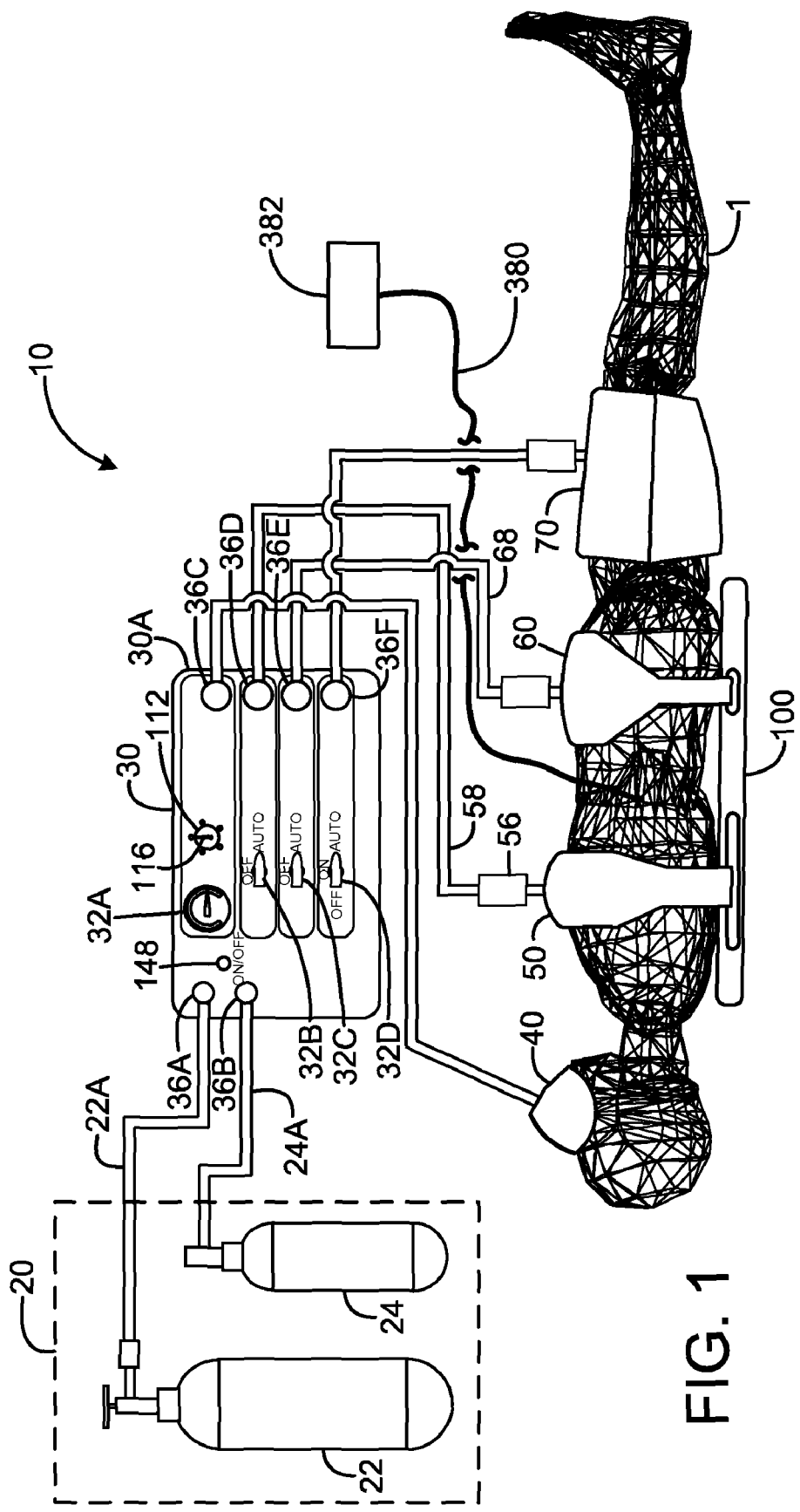
FIG. 1 is a schematic drawing illustrating elements of an exemplary embodiment of a portable resuscitation system in place on a person.

In the following detailed description and in the several figures of the drawing, like elements are identified with like reference numerals. The figures are not to scale, and relative feature sizes may be exaggerated for illustrative purposes.

An exemplary embodiment of a resuscitation/respiration apparatus in accordance with aspects of the invention is adapted for portable use, e.g. by emergency medical technicians or other first responders, or others. This embodiment is powered by a small battery and utilizes compressed gas as found in typical fireman's breathing apparatus and medical oxygen as used by emergency teams.

An exemplary embodiment may be simplified by the elimination of adjustments such as flow, cycle rate and pressure controls, which are factory set for optimum performance. In other embodiments, some or all these parameters may be adjustable by the user. An exemplary embodiment may utilize an integrated ventilator that is simple to operate and may be synchronized with operation of inflatable cuffs for chest, abdomen and leg compression, as described below.

The American Heart Association recommends that cardiopulmonary resuscitation (CPR) be provided for 20 minutes or until the patient is resuscitated, whichever comes first. In an exemplary embodiment, an air injection system dilutes the compressed air with ambient air, providing more than 20 minutes of operation, and in one embodiment approximately 30 minutes, from a full firemen's air cylinder filled to 4500 PSI.

An exemplary embodiment of the system, adapted for portable use, may be housed in a shock and water resistant container that may be carried or worn as a back-pack. The inflation cuffs may be mounted on a backboard in a ready position for immediate application to the patient.

FIG. 1 is a schematic drawing illustrating elements of an exemplary embodiment of a resuscitation/respiration system 10 in place on a reclining patient 1. The system 10 includes a cylinder 22 of compressed air, a cylinder 24 of breathing oxygen, a system unit 30, a ventilator mask 40, a chest cuff 50, an abdomen cuff 60, and leg cuff garments 70. The cuffs have inflatable bladders that are held in place by straps with hook and loop fasteners. They are attached to a backboard 100 for easy positioning. The cylinders 22, 24 are connected to the system unit 30 by air lines/hoses and connectors. Air lines are attached from the system unit to the cuffs with connectors.

The system unit 30 in an exemplary embodiment has six connector ports 36A, 36B, 36C, 36D, 36E and 36F configured for removable engagement with the respective air hoses. Connector port 36A is attachable to the hose 22A attached to the air cylinder 22. Connector port 36B is configured for attachment to hose 24A attached to the oxygen cylinder 24. Connector port 36C is configured for attachment to a hose attached to the face mask 40 of a patient ventilator module. Connector port 36D is configured for attachment to hose 58 attached to the chest cuff 50. Connector port 36E is configured for attachment to hose 68 attached to the abdomen cuff 60. Port 36F is configured for attachment to a hose attached to the leg cuffs 70.

In an exemplary embodiment, the system unit 30 includes a meter 32A depicting the airway pressure supplied to the ventilator mask, and a manual control 112 with control knob 116 which allows manual control of several patient tidal volume settings, as well as a "demand" setting. The "demand" position is essentially an "off" mode so that oxygen is only provided when demanded by the patient. The valve is set by rotating the knob 116 to a demand position. Valves 32B, 32C and 32D have control handles on the control panel of the system unit 30, and control the bleed flow to the air module reference chambers (described below) for the respective chest, abdomen and leg cuffs. Valves 32B and 32C can be turned to the OFF or AUTO positions. In the OFF position, the valve is closed, and does not allow flow to the respective cuff. In the AUTO position, the flow is controlled automatically by a timer module (described below) opening and closing solenoid valves in the corresponding circuits. Valve 32D is a 3-way valve, for controlling pressure applied to the air module reference chamber for the leg cuff. This valve has OFF and AUTO positions as described above for valves 32B and 32C, and also has an ON position. In the ON position, the flow is on, so that a constant pressure is applied to the leg cuff.

The system unit 30 in an exemplary embodiment includes a rechargeable battery, and is small and light enough for ready portability, in an application suitable for portable use.

Figure 1A:
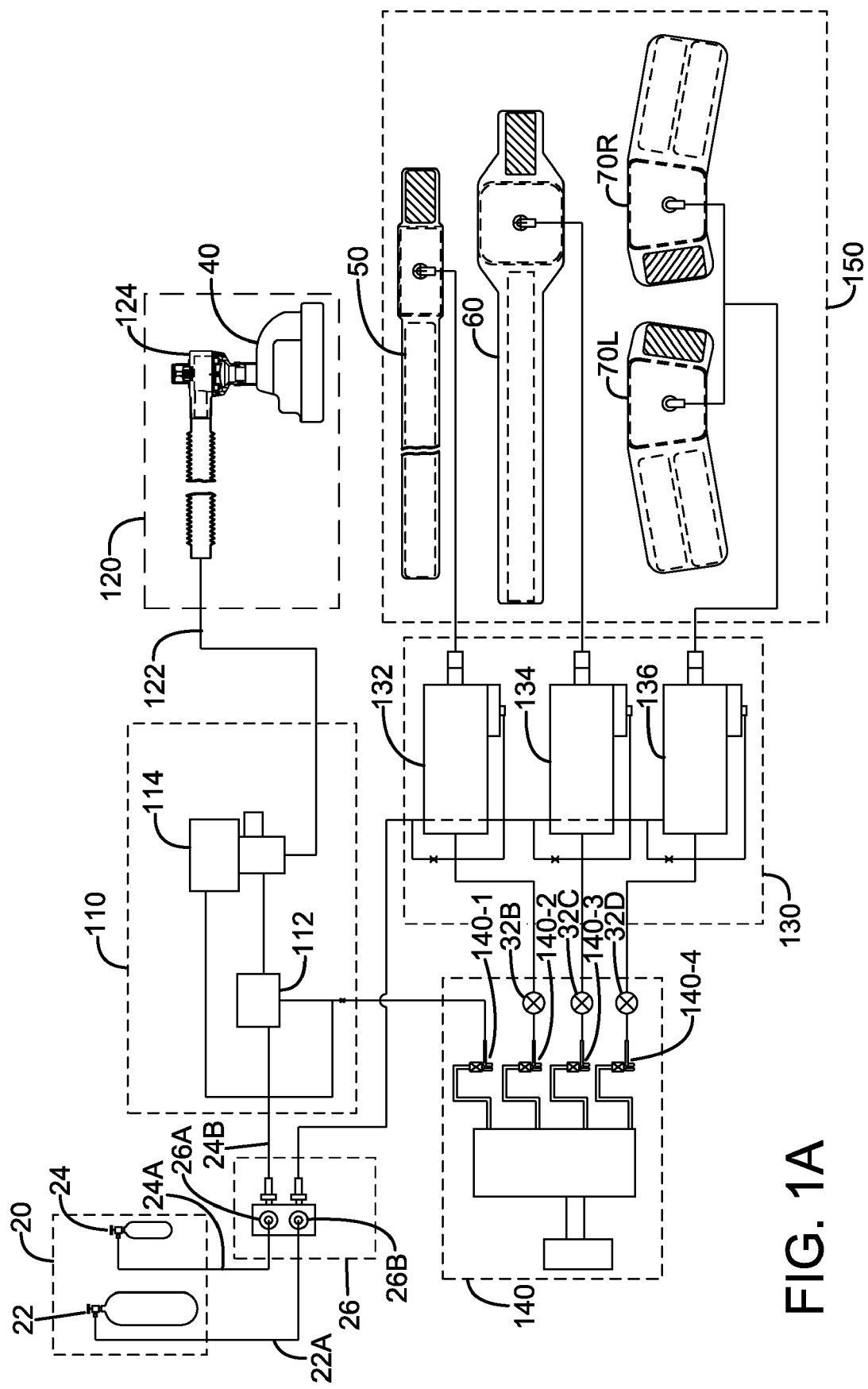
FIG. 1A is a schematic view of an embodiment of a portable resuscitation system.

The portable resuscitation system 10 includes several modules, as illustrated in the schematic view of FIG. 1A. One module is the tank module 20 that includes an air cylinder and an oxygen cylinder. Each cylinder has an attached regulator that is set to provide the proper pressure output to the rest of the system.

The module 20 is connected by air and oxygen lines 22A, 24A to an input module 26. In an exemplary embodiment, this module has connectors 26A, 26B that conform to a diameter indexed safety system, developed by the Compressed Gas Association, known as a DISS system, that prevents the lines from being connected incorrectly. In this exemplary connector system, non-interchangeable indexing is achieved by a series of increasing and decreasing diameters in the components of the connections. These specific diameters act in a key-like fashion, so the fittings within one gas service family will connect only with their own family members. Other types of connectors may alternatively be employed. The module 26 also contains pressure regulators that further adjust the pressures for close control of supply pressure to the other modules.

Oxygen is supplied to ventilator supply module 110 by line 24B. This module includes a tidal volume control 112 and a demand regulator 114. In an exemplary embodiment, the tidal volume control 112 has five positions for various levels of tidal volume, which are set by knob 116 on the control panel of the system unit 30. Each position is calibrated for a flow that, when matched with the actions of the timer module, allows for a fixed volume of gas to flow to the outlet of the demand regulator 114. At any time that the patient demands more flow than the tidal volume control 112 puts out, the demand regulator will provide this flow in response to this demand. Thus, if the patient demands more flow than is delivered by the tidal volume control, it will result in the mask pressure becoming negative. This will trigger the demand regulator to add gas so as to maintain only a slight negative pressure.

A patient ventilator module 120 includes a hose 122 connected to the demand regulator 114, a patient valve 124 and the patient mask 40. The hose 122 delivers output from the ventilator module 110 to the patient. The hose is collapsible for easier storage and the patient valve 124 is equipped with an inhalation/exhalation valve that prevents re-breathing of expired gas. The valve 124 may also be equipped with an alarm whistle that sounds a tone when pressure in the outlet exceeds a threshold pressure, e.g., 55 cm of water.

Air module 130 includes three air pressure modules 132, 134, 136 to control the flow of air to the inflatable bladders in each cuff 50, 60, 70L and 70R. Regulated air is supplied to the module inlets through a manifold. The air module has a pressure regulator to set the outlet pressure for the cuff bladders. For each cuff, inlet pressure is fed through a restrictor to a diaphragm chamber in the regulator that sets the outlet pressure. A solenoid valve in the timer module opens and closes to turn the regulator on and off. The reference pressure is sensed by a compensated exhaust valve that operates to deflate the cuff bladders in proper sequence and serves as a relief valve to protect against overpressure.

A timer module 140 includes circuitry that sets the proper sequence and timing of solenoid valves to control both the air modules and the ventilator operation. The module 140 is preferably operated by a rechargeable battery power source in an exemplary embodiment.

A cuff module or kit 150 includes the cuffs 50, 60 and 70L-70R, which respectively include inflatable bladders for "chest", "abdomen" and "legs".

Figure 2:
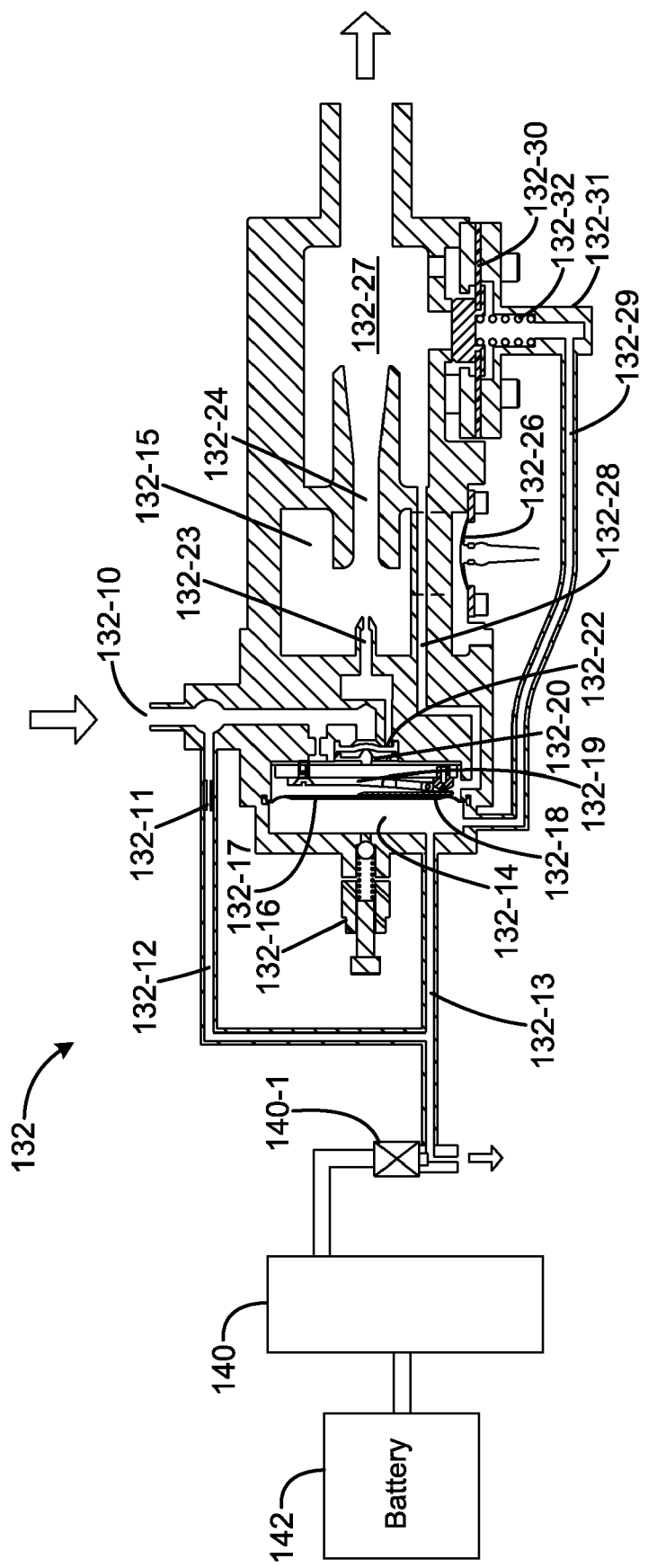
FIG. 2 is a schematic drawing of an exemplary embodiment of one of three modules in the system of FIG. 1A that control the flow of air to and from the chest, abdomen and leg inflation cuffs.

FIG. 2 is a schematic drawing of an exemplary one (132) of three modules 132, 134, 136 that control the flow of air to and from the chest, abdomen and leg inflation cuffs 50, 60, 70. Compressed air from tank 22 is introduced at port 132-10. A restrictor 132-11 allows a small bleed via channel 132-12 to branch 132-13 to chamber 132-14. When solenoid valve 140-2 is closed by timer module circuit 140, the pressure in chamber 132-14 increases until relief valve 132-16 opens to maintain a preset pressure in chamber 132-14. This pressure acts against diaphragm 132-17 to depress paddle 132-18, which in turn opens pilot valve 132-19. This reduces the pressure on holding the main valve 132-22 closed, and initiates flow through the nozzle 132-23. The nozzle flow is directed to the throat 132-24. The high velocity of the nozzle flow causes the pressure in chamber 132-25 to drop so as to open check valve 132-26 and entrain ambient air. The pressure in outlet chamber 132-27 is sensed through passage 132-28 so as to cause the pressure on the diaphragm 132-17 to balance the reference pressure in chamber 132-14 and thus allow the pilot valve 132-19 to close and shut off the flow. The pressure in chamber 132-14 is sensed through line 132-29 by diaphragm 132-30 in the compensated discharge valve 132-31. A spring 132-32 biases the valve to a closed position so that when the pressure at the outlet is a small amount (e.g., approximately 25 mm Hg.) higher than the reference pressure (in chamber 132-14) the valve opens and relieves the pressure in the outlet. This allows the compensated valve 132-31 to act both as a relief valve and as an exhaust valve. Retaining pressure in the cuff bladders (e.g. 25 mm Hg) has two advantages. It increases peripheral resistance in the patient's circulatory system and reduces air consumption by preventing complete deflation of the inflation cuffs. The timer module 140 exhausts the reference pressure in chamber 132-14 through solenoid valve 140-2; this in turn causes the compensated valve 132-31 to open and exhaust the cuffs. The solenoid valve 140-2 is open to allow flow from chamber 132-14 to the ambient.

Thus, the air module 132 operates in the following manner. Compressed air is supplied to port 132-10, which in turn flows to a diaphragm valve 132-22 in the regulator assembly. This diaphragm is held closed by the pressure in chamber 132-20 which is pressurized by inlet pressure through restrictor 132-21. Pilot valve 132-19 acts to seal this chamber through a spring biased paddle assembly 132-18. One side of the diaphragm senses the pressure in the outlet chamber 132-27 through passage 132-28 while the other side senses the reference pressure in chamber 132-14.

When the pressure at the outlet chamber 132-27 drops below the reference pressure in chamber 132-14, the diaphragm 132-18 moves to open the pilot valve 132-19 which in turn causes the diaphragm valve 132-22 to open and permit flow from the inlet 132-10 to flow through nozzle 132-23 to the outlet chamber 132-27. This flow enters the throat 132-24 at high velocity resulting in the pressure in chamber 132-25 dropping below ambient pressure due to the Bernoulli effect which in turn initiates flow of ambient air through check valve 132-26 into mixing chamber 132-25. This operation thus is provided by an ambient air injection system which dilutes the pressurized air from the cylinder 22, and thus prolongs the operation of the system and its chest, abdomen and leg cuffs from the compressed air cylinder.

Figure 3:
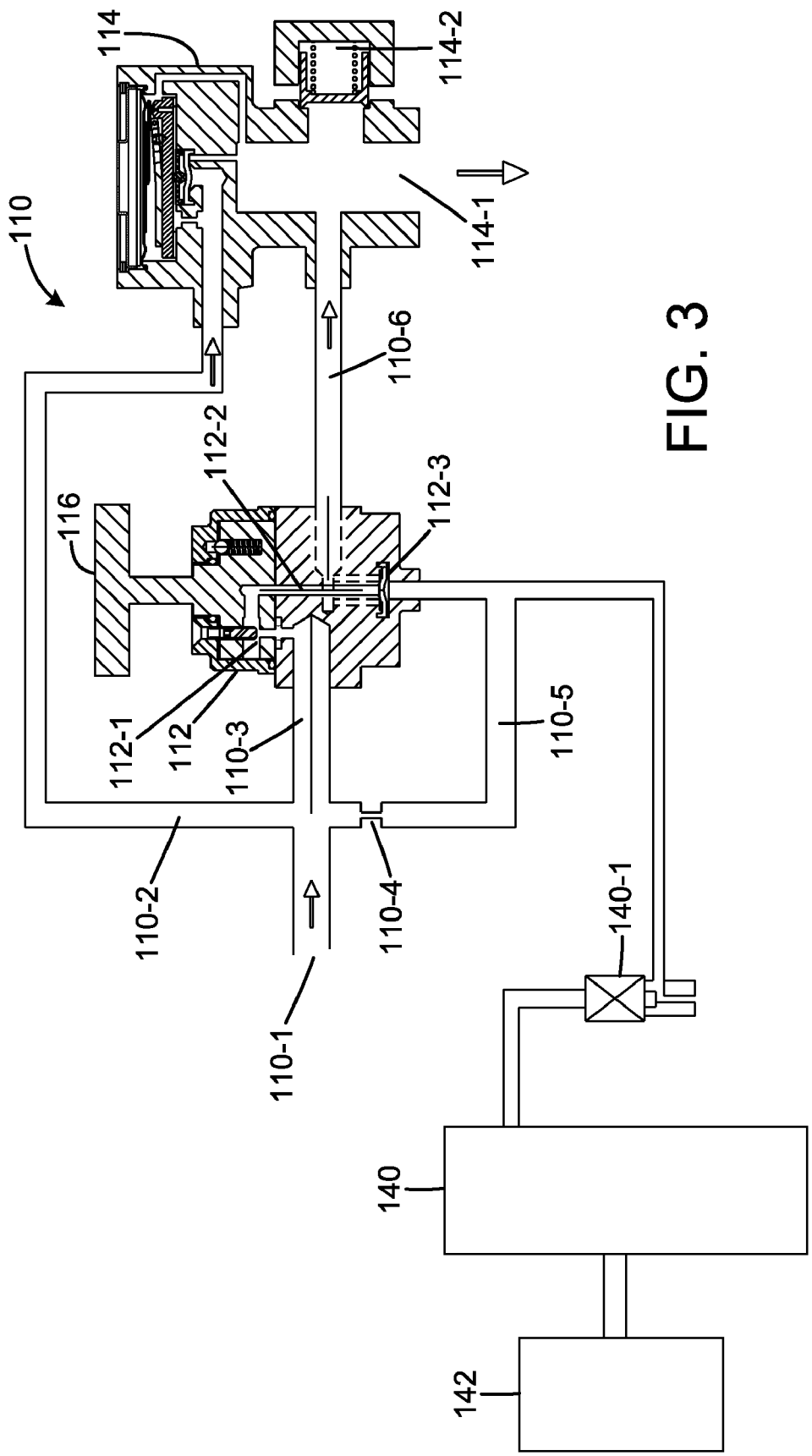
FIG. 3 is a schematic of a ventilator circuit formed by the ventilator supply module of the system illustrated in FIG. 1A.

FIG. 3 is a schematic of the ventilator circuit formed by the ventilator supply module 110 of the system 10. The ventilator module has an oxygen inlet port 110-1. Pressurized oxygen is introduced to port 110-1 and passed through bypass channel 110-2 to demand regulator valve 114. Simultaneously it is ported to the tidal volume control 112 through channel 110-3. The tidal volume control 112 contains a series of orifices 112-1, which may be adjustable restrictors, which limit the flow through passage 112-2 to diaphragm valve 112-3. A restrictor 110-4 allows a small bleed through passage 110-5 to the opposite side of valve 112-3 so that the opening and closing of valve 112-3 is responsive to solenoid 140-1. When solenoid 140-1 is closed, valve 112-3 is biased closed, and when valve 140-1 is open, valve 112-3 is opened to allow flow through outlet passage 110-6 to the outlet 114-1 of the demand regulator 114. The opening and closing of the solenoid valve 140-1 is controlled by the timer module 140. Thus, pressurized oxygen is bled through restrictor 110-4 and through channel 110-5 to hold the valve 112-3 in a closed position until solenoid valve 140-1 is opened by the timer module 140, at which time the pressure in line 110-5 is exhausted and valve 112-3 is opened to port flow through channel 110-6 to the demand valve outlet 114-1 which provides a ventilator outlet port. Demand regulator 114 is a servo valve similar to that described above in FIG. 2. When the pressure in the outlet of the demand regulator 114 becomes negative, the demand regulator 114 responds to supply oxygen to the outlet 114-1. If the pressure at the outlet exceeds a prescribed maximum limit, a relief valve 114-2 will open and bleed off excess oxygen, preventing the oxygen flow to the patient circuit from exceeding safe limits.

The ventilator circuit operates in the following manner. Pressurized oxygen flows into port 110-1 and is channeled directly to the demand regulator 114 through channel 110-2. It is also ported to the tidal volume control 112 through channel 110-3. Regulated pressure is fed through restrictor 110-4 and passage 110-5 to diaphragm valve 112-3. This channel may be vented through solenoid valve 140-1 in automatic mode which allows diaphragm valve 112-3 to open and cause a flow to outlet channel 110-6. The flow is restricted by one of four adjustable restrictors 112-1, which is positioned by rotating knob 116, so as to limit the flow to the valve 112 outlet and thus with the timer 140 determine the volume of gas flowing to the patient.

Figure 3A:
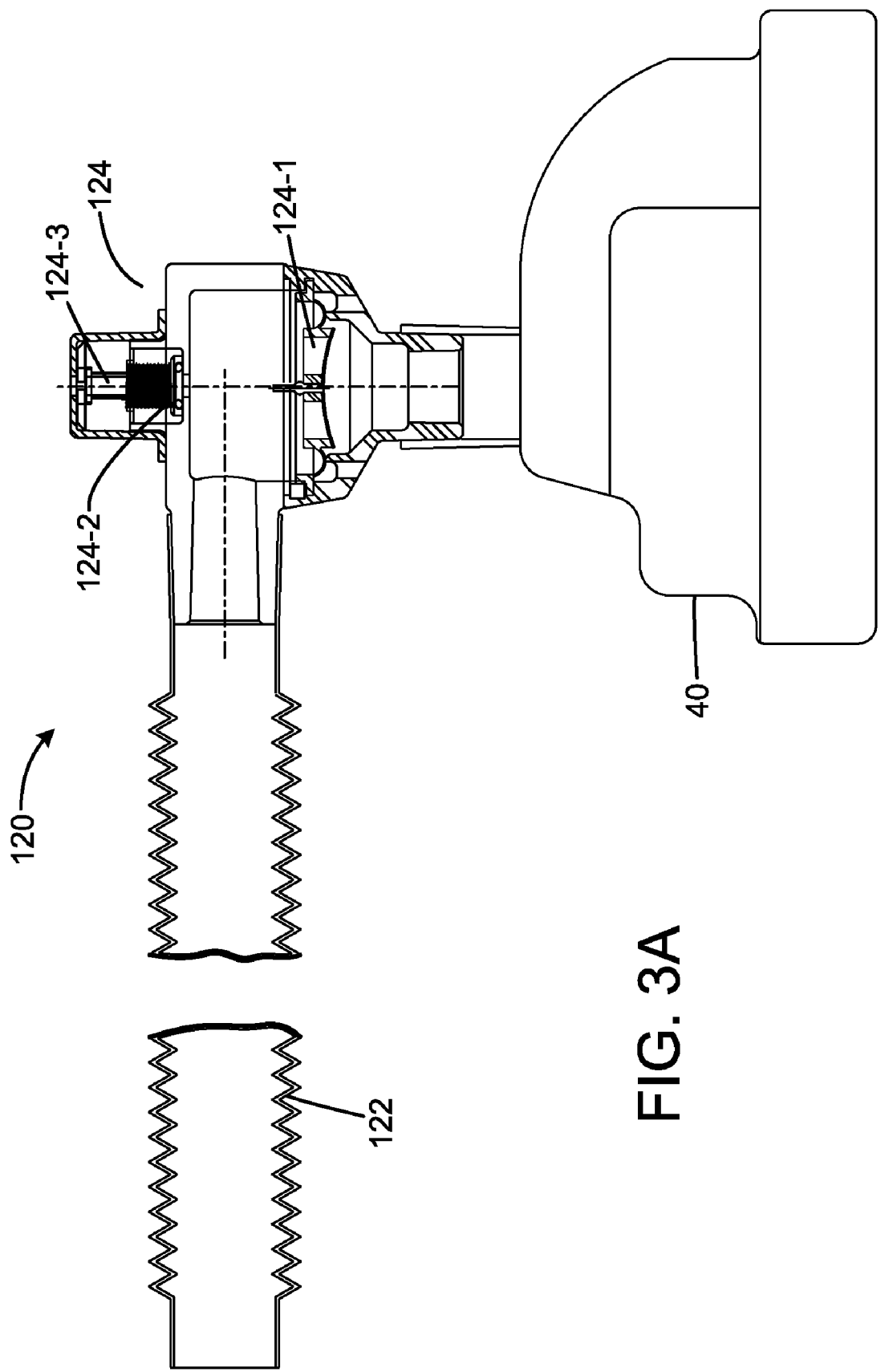
FIG. 3A depicts an exemplary embodiment of a disposable patient circuit or module of the system of FIG. 1A.

FIG. 3A depicts an exemplary embodiment of a disposable patient circuit or module 120. The module connects to the ventilator outlet port 114-1 of the controller and delivers breathing gas to the patient. The patient circuit includes a hose 122, a patient valve 124 and a mask 40. The patient valve 124 includes an inhalation/exhalation valve 124-1, a relief valve 124-2 and a whistle 124-3. When the pressure in the mask exceeds a threshold pressure, e.g., 55 cm. of water, the relief valve will open to prevent the pressure from rising further. The gas from the relief valve operates an audible alarm, in this example the whistle 124-3, to alert the care-giver that the patient's airway is blocked and requires attention.

Figure 4:
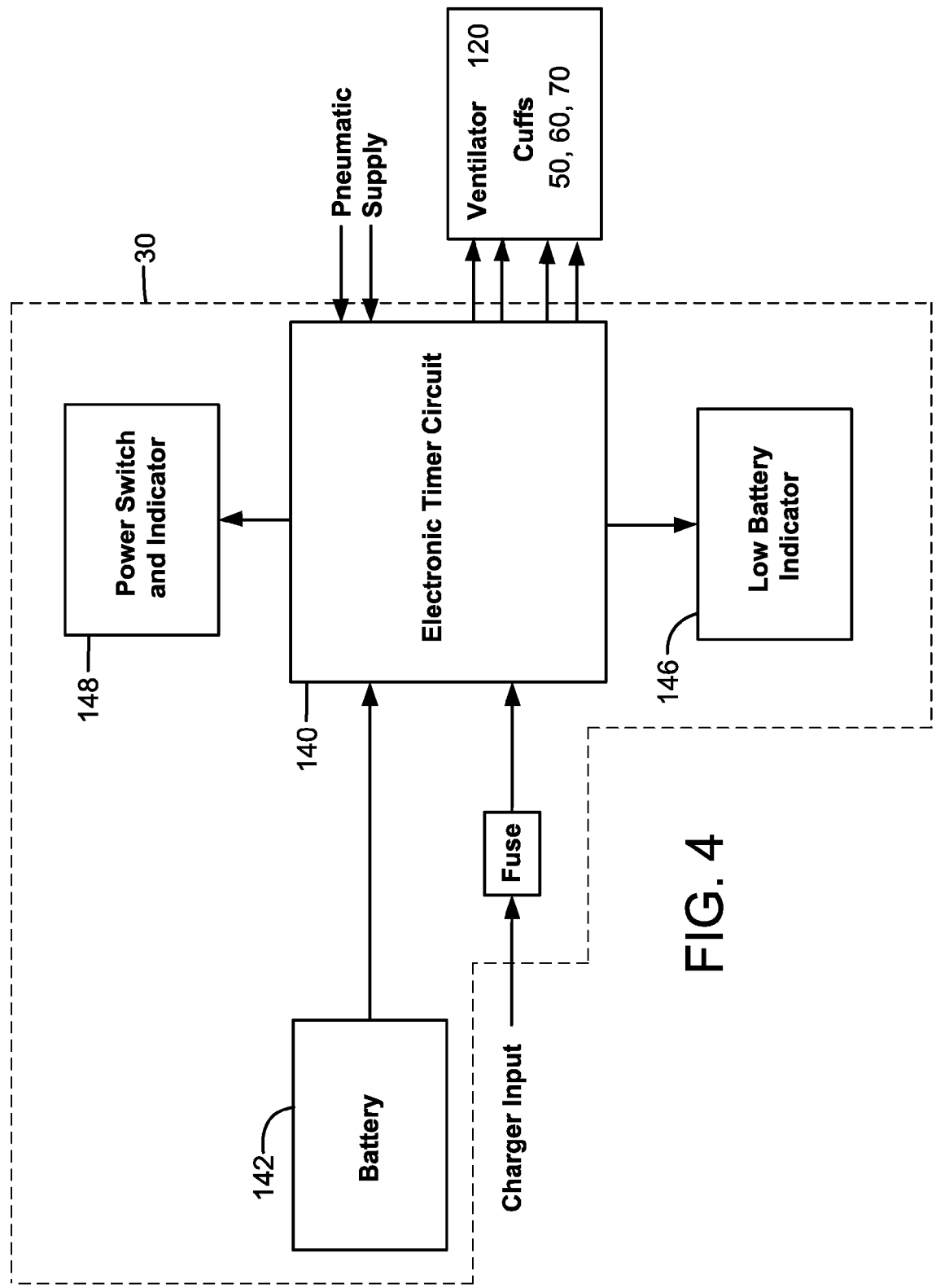
FIG. 4 is a simplified block diagram of an exemplary embodiment of the control unit of the system of FIG. 1.

FIG. 4 is a general schematic block diagram illustrating elements of the system unit 30. The system unit is housed in a metal cabinet or enclosure, and includes an electronic timer circuit or module 140, a power switch 148 for turning the unit on/off, and six connectors for connection to the pneumatic supply (i.e. the tank 20 and oxygen tank 22), the ventilator mask and cuffs 50, 60, 70. A rechargeable battery 142 is mounted within the cabinet to power the timer module 140. A connector is provided for electrical connection of a battery charger to the system unit 30 to charge the battery 142 through a fuse.

Figure 4A:
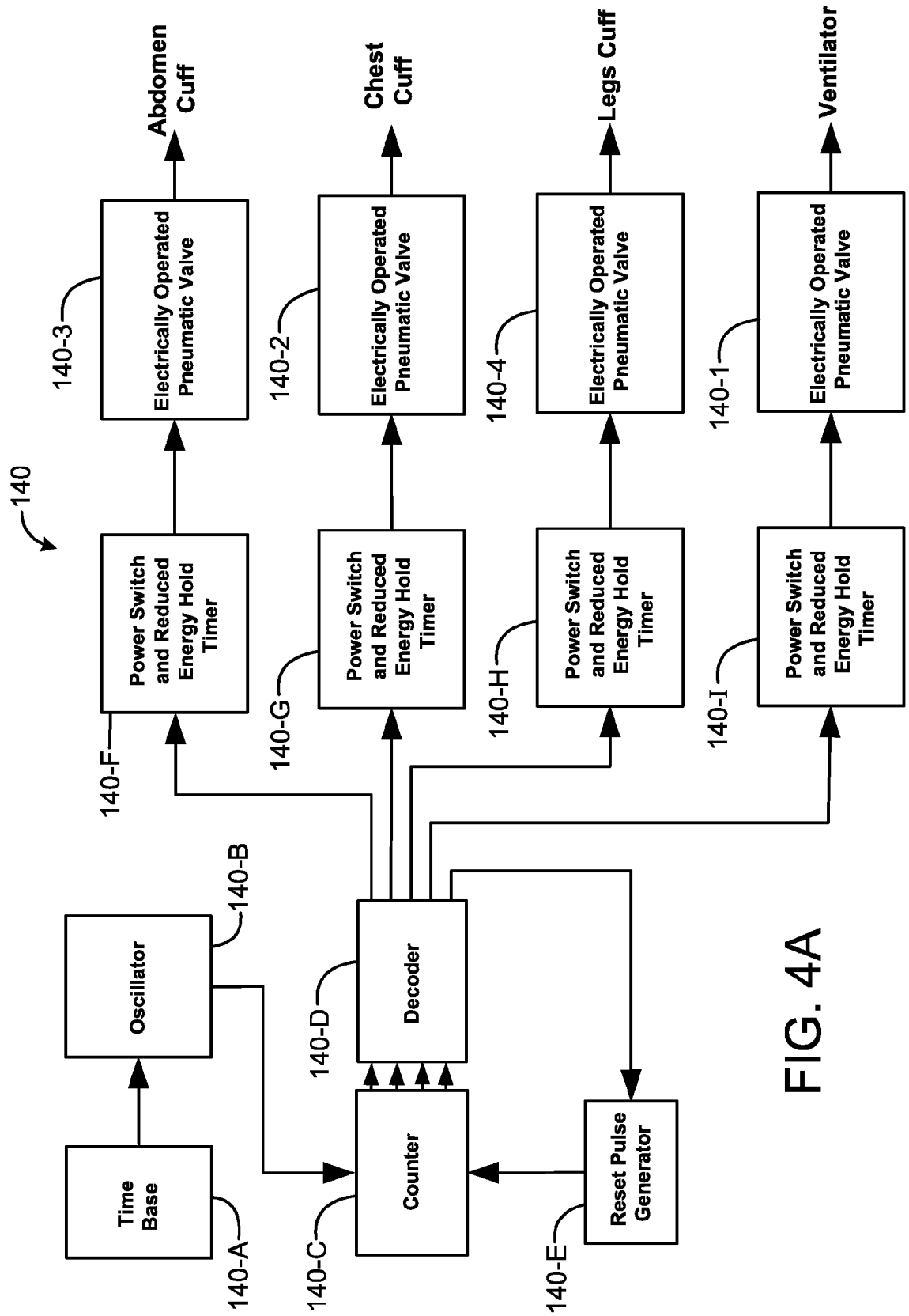
FIG. 4A is a simplified functional block diagram of an exemplary embodiment of the timer module of the system of FIG. 1A.

Referring now to FIG. 4A, a simplified functional block diagram of an exemplary embodiment of the timer module 140 is illustrated. The timer module 140 includes circuitry for implementing several functions, including: Time Base 140-A, Oscillator 140-B, Counter 140-C, Decoder 140-D, Reset Pulse Generator 140-E, Power Switch and Reduced Energy Hold Timer functions 140-F, 140-G, 140-H, 140-I which control the electrically operated pneumatic valves 140-3, 140-2, 140-4 and 140-1. The respective pneumatic valves control air/oxygen delivery to the abdomen, chest and leg cuffs 50, 60 and 70, and to the ventilator module 110.

The time base 140-A provides a means for the oscillator 140-B to produce an accurate, stable frequency. The time base may be achieved, for example, with a crystal or ceramic resonator, or combinations of resistor-inductor-capacitor networks depending on the requirements of the system. A resistor-capacitor (R-C) circuit is utilized in an illustrative implementation.

The oscillator 140-B produces an electrical timing reference utilizing the electrical characteristics of the time base 140-A. It may be implemented with three gate elements, or, in an exemplary embodiment, by a ripple-carry counter-divider (U1), FIG. 4B.

The counter 140-C and decoder 140-D essentially count the timing reference pulses produced by the oscillator and produces electrical outputs when appropriate counts have been achieved. Depending on the implementation, the counter may be reset to a known value when a full cycle count has been achieved. In other implementations, resetting of the counter may be inherent and unnecessary, if the total count is $2^n$, for example. One exemplary implementation uses a ripple-carry counter and multi-input gates to decode the count registers. CMOS logic elements are used but the implementation may be accomplished with TTL, or any other logic family including the use of a read-only memory or a microprocessor.

The outputs of the decoder 140-D drive the power switches 140-F . . . 140-I which supply current to the electrically operated pneumatic valves 140-1, 140-2, 140-3 and 140-4. The input signals to the power switches are at a very low power level. When switched ON, the power switches provide the current necessary to operate the pneumatic valves. Additionally, in an exemplary embodiment, the power switches include a circuit to provide high pull-in drive to the valves and then reduce the drive current to that necessary to sustain their powered position.

As described above, the electronic timer module 140 controls the timing and valve operation of the system 10. It includes a battery powered digital controller to implement a specified operational sequence. In an exemplary embodiment, the control is provided by a hardware-based state-machine which sequences the system through 12 discrete operational states (Table I) before resetting and repeating.

TABLE 1

Timer States

| STATES | 1 | 2 | 3 | 4 | 5 | 6 | 7 | 8 | 9 | 10 | 11 | 12 | RESET |
|---|---|---|---|---|---|---|---|---|---|---|---|---|---|
| CHEST | ON | OFF | ON | OFF | ON | OFF | ON | OFF | ON | OFF | ON | OFF | ON |
| ABDOMEN | OFF | ON | OFF | ON | OFF | ON | OFF | ON | OFF | ON | OFF | ON | OFF |
| VENTILATOR | OFF | ON | OFF | OFF | OFF | ON | OFF | OFF | OFF | ON | OFF | OFF | OFF |
| LEGS | OFF | OFF | OFF | OFF | OFF | OFF | OFF | OFF | OFF | OFF | ON | ON | OFF |

Table 1 shows the twelve states of the counter-divider, and the operational status of each pneumatic solenoid in the respective states. In an exemplary embodiment, the duration of each state is about one (1) second. Table 1 also shows a thirteenth or reset state. The reset state is a very brief period when the counter is returned to State 1. The duration of the reset state in an exemplary embodiment is less than 1 millisecond, or less than 0.1% of the duration of each of the other states. After completion of State 12, the timer enters the Reset State. The timer logic is configured so that the solenoid valve outputs in the Reset State are the same as State 1, so that the cuffs function as they do in State 1, and the Reset State is not functionally discernable in the operation of the equipment. Once reset is complete, the timer enters State 1. There is no transition effect on the cuffs other than a 0.1% stretch of the State 1 condition to complete reset.

In an exemplary embodiment, the timer module may be implemented with CMOS logic elements and does not utilize a microprocessor or software to achieve this function. The use of CMOS components results in extended battery-powered operation due to their low current demand. In addition, operation at 12V achieves noise immunity in excess of 2V.

Figure 4B:
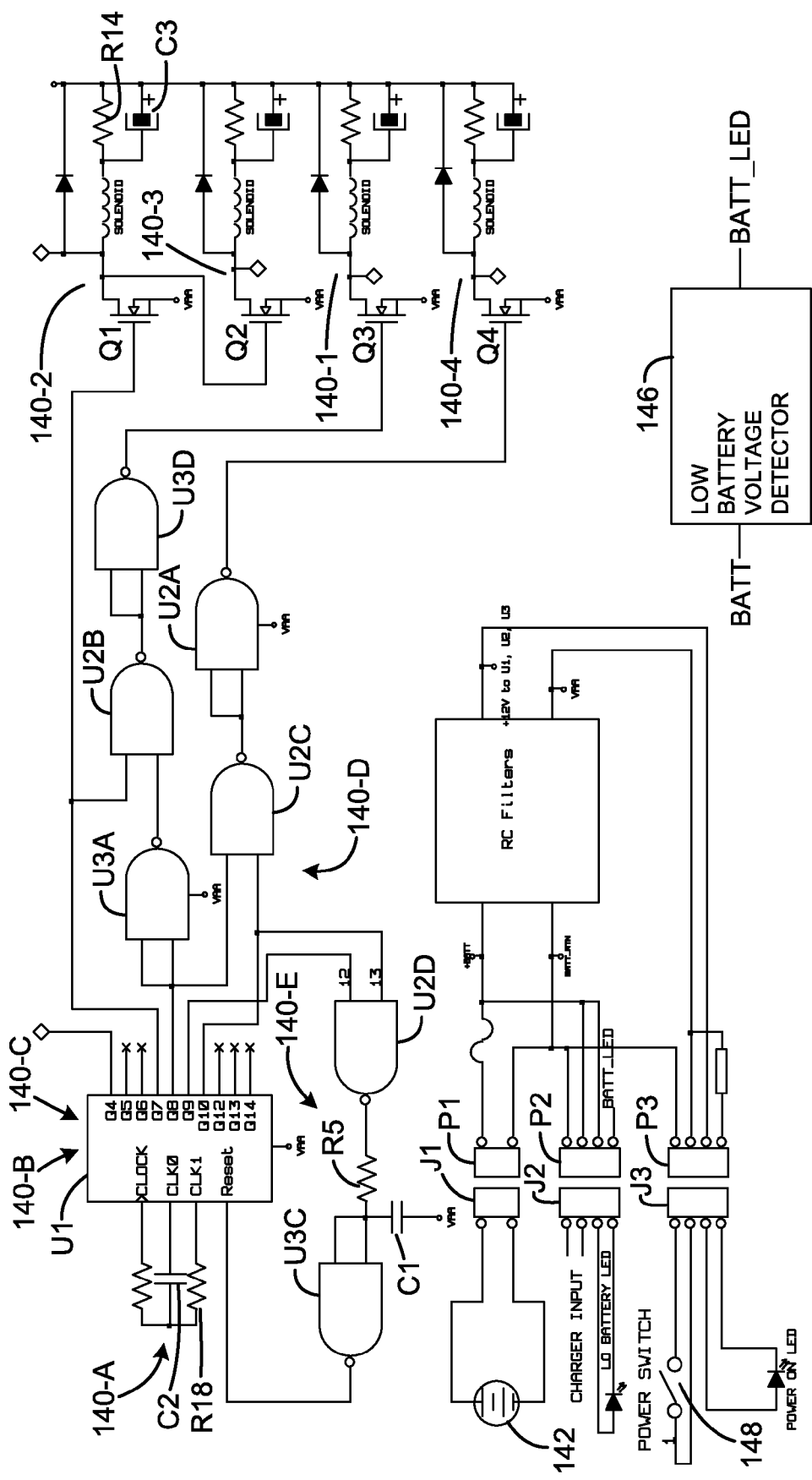
FIG. 4B illustrates an exemplary circuit implementation of the timer module.

FIG. 4B is a schematic diagram illustrative of circuitry of an exemplary embodiment of the timer module 140. In this embodiment, the primary timing function is provided by a resistor-capacitor (RC) (R18, C2) controlled oscillator and a ripple-carry counter-divider (U1). A worst case timing tolerance of less than +/−5% considering components, temperature, and supply voltage is expected by the use of R and C components with tolerances of 1% and 2% respectively. Decoding of the timing states is accomplished by several 2-input NAND gates (U2A, U2B, U2C, U3A, U3D) with Schmitt trigger outputs, such as type 4093 NAND gates circuits. The Schmitt trigger outputs further increase the noise immunity of the circuit and improve the reset pulse generation.

Reset of the Counter-Divider 140-C is provided by the Reset Pulse Generator 140-E (FIG. 4A). In an exemplary embodiment illustrated in FIG. 4B, the Reset Pulse Generator may be implemented by resistor R5, capacitor C1, and inverter U3C. The Reset Pulse Generator 140-E responds to the decoding and detection of a count in excess of the objective twelve states which occurs when both inputs to NAND gate U2D are concurrently high. The high inputs to gate U2D result in a low output to R5 and ultimately to U3C after a delay due to the R5-C1 time constant. U3C is a gate which has a Schmitt trigger input and functions as an inverter because both inputs are tied together. The low input of U3C results in a high input to the Counter-Divider, U1, which resets its count to State 1 and forces all of its outputs low. Once the inputs to U2D are set low, its output becomes high. After the effect of an R5-C1 time constant, the output of U3C is driven low, removing the reset of U1 and allowing it to proceed through the objective twelve states. Properly resetting U1 involves a salient condition that the reset input must be asserted for a minimum time interval. This requirement is achieved by the R-C circuit and Schmitt trigger gate U2D. There is no assurance that the reset is complete when the two inputs to U2D are zeroed. But the R-C circuit and Schmitt trigger gate assure that the reset remains asserted for the required time after the inputs to U2D are zeroed.

Without the hysteresis of the Schmitt trigger, there is essentially little control of the reset duration and a "race" will exist in the reset circuit. U2D reacts immediately to its two high inputs and charges C1 through R5 to the trip level of U3C. Once the output of U3C goes high, reset is immediately asserted, forcing of the inputs to U2C low and its output high. Now C1 is discharged through R5 to the trip level of U3C. The time duration of the reset assertion is the sum of the time for the reset to return the output of U2D high and the time required to discharge C1 sufficiently to return to the trip level of U3C. The former is a function of the gate speed and is very short. The latter time is determined by the charge that C1 has attained during reset pulse which now must be removed to reduce the input of U3C to the trip level. In a typical gate with no input level hysteresis, the charge interval of C1 and resulting charge is very small because it is determined by the reset time of two outputs of U1 and the propagation delay of U2D, both of which are very short compared with the required reset duration. The hysteresis of the Schmitt trigger gate requires that C1 discharge from the high trip level to the low trip level before the reset is terminated. These voltage levels along with the RC parameters reliably assure controlled reset duration in excess of 100 times that required with a minimum of components.

In an exemplary embodiment, a low battery level detector circuit 146 is included to monitor the battery voltage. This circuit is powered continuously by the battery 142 and flashes an indicator LED 146A when the battery discharges to a level insufficient for more than 45 minutes of operation. The flashing function results in asymmetric flashing, ON time less than OFF time, to reduce power consumption while achieving an attention demanding visual effect. The level detection circuit may be implemented using a dual, low power comparator, and preferably draws little current, e.g. less than 2 mA, from the battery during monitoring.

The interface between the electronic control circuit and the pneumatic module 130 is provided by four solenoid valves (140-1, 140-2, 140-3, 140-4). The valve coils are driven by power MOSFET's (Q1, Q2, Q3, Q4). The power MOSFET's interface well with the CMOS gates because they can operate from the low steady-state drive current available from the gates and have very low resistance in the ON state to drive the solenoid valves without dissipation losses in the switches. In addition, the limited current available from the gates combined with the large gate capacitance of MOSFET's results in a switching speed limitation, often considered a problem. Here it is an advantage because the reduced switching speed softens the valve transitions and renders them unresponsive to switching transients resulting from minor skew of the ripple counter outputs.

Decoding from a single time base maintains the operating relationship between the body cuffs and ventilator independent of the operating frequency.

Figure 5A:
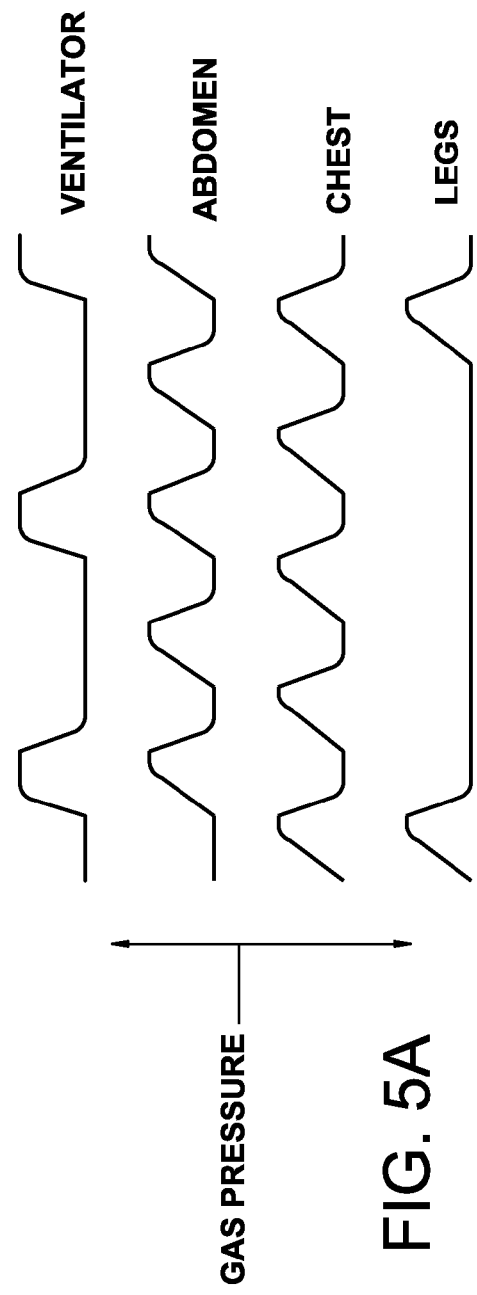
FIG. 5A is a graph illustrating control of gas pressure to the ventilator and cuff bladders in an exemplary embodiment.
Figure 5B:
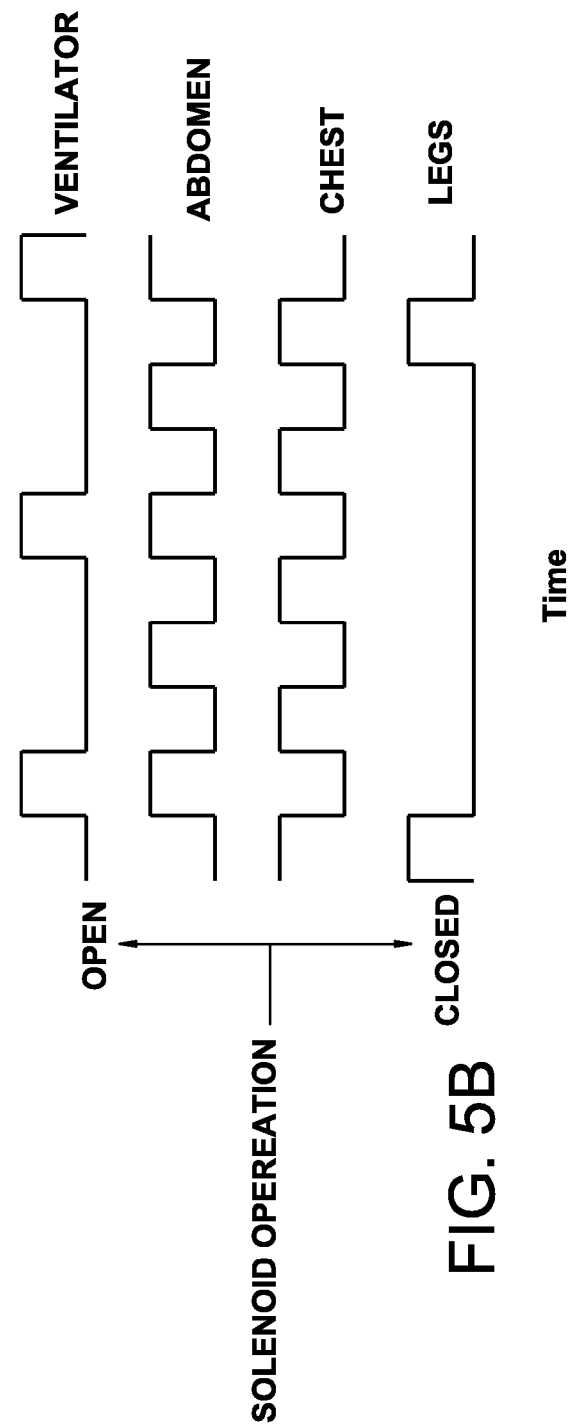
FIG. 5B illustrates operation of the corresponding solenoid valves to provide the gas pressure control illustrated in FIG. 5A.

FIGS. 5A and 5B illustrate graphically the gas pressure (FIG. 5A) resulting from operation of the timer module and solenoid valve operation. Thus, the relative pressures in the cuff bladders and ventilator circuit resulting from the opening and closing of the controlling solenoid valves are illustrated. In an exemplary embodiment, the chest bladder pressure is in counter phase to the abdominal bladder giving the interposed abdominal compression (IAC)-CPR effect. The leg bladders cycle on every fifth cycle of the chest bladder. The ventilator is synchronized with the abdominal bladder to eliminate the possibility of insufflations of the stomach. Thus the ventilation and compression can be carried on without interruption. In an exemplary embodiment, each abdomen and chest cycle have durations of one second on and one second off in counter phase.

Very low thermal dissipation of the timer is achieved by the use of MOS technology components. This is a two-fold advantage because battery power is conserved for longer operation and component temperatures remain near ambient levels. In addition, valve driver RC circuits for each valve, R14 and C3 for valve 140-2; R15 and C4 for valve 140-3; R16 and C5 for valve 140-1; R17 and C6 for valve 140-4, reduce the power provided to the solenoid valves to an approximate 66% maintenance level once the solenoid is seated, again reducing battery drain and component heating. In an exemplary embodiment, each solenoid valve dissipates less than 0.5 W average.

In an exemplary embodiment, the battery 142 is a sealed lead-acid unit. It is charged via an external charger through a connector mounted on the control unit 30. A line mounted fuse limits the charge circuit current to 0.5 A. The circuit board includes a resettable 0.375 A fuse to limit battery current. A unidirection 15V, 1500 Watt transient suppression diode is also included on the circuit board. It, with the circuit fuse, provides protection from applied transient voltages in excess of approximately 18V and reverse polarity voltages. The fuse resets itself after the excessive current condition has been removed for several minutes. The unit may be powered directly by the charger or may be operated while the battery is being charged.

The circuit board is interfaced with the power inputs and operating controls via three connectors. Each of the connectors (P1, P2, P3) is different and keyed so that they may not be inadvertently installed incorrectly.

In an exemplary embodiment, the circuit is designed to tolerate an electrically noisy environment resulting from high frequency communication radios. It is also housed in an aluminum enclosure (Faraday cage) to attenuate potential electrical interference. The internal clock oscillator operates at 64 Hz and at low power levels to preclude the emission of high frequency EMI.

While an exemplary embodiment of the timer module is implemented as an electronic circuit, with electrically operated solenoid valves to operate the air pressure modules and the ventilator module, these elements may be implemented by pneumatic circuits in other embodiments. These pneumatic circuits may be operated by the pressurized gas supplies.

Figure 6:
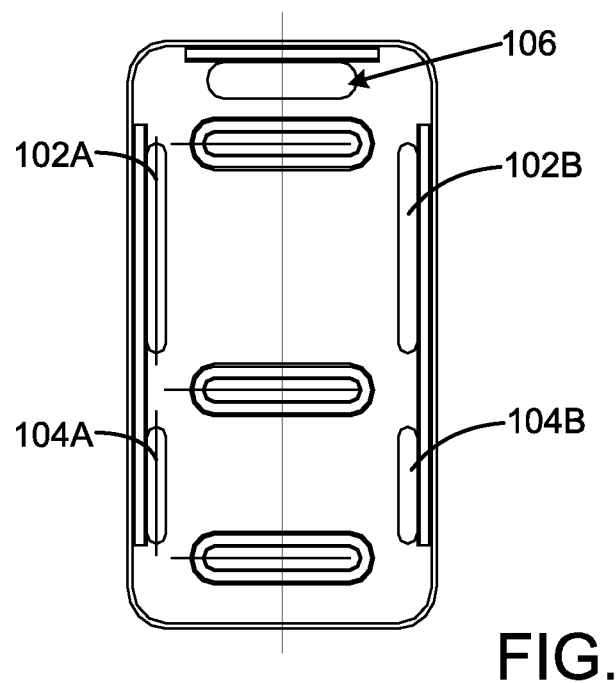
FIG. 6 is a top plan view illustrating an exemplary embodiment of a backboard suitable for use in combination with the system of FIG. 1.

The system 10 may include a backboard 100 to support the patient where needed, (such as on a bed) and accommodates the chest and abdominal compression cuffs 50 and 60 (FIG. 1). The cuffs may be mounted on the board so as to facilitate placement on the patient and speed of donning. In an exemplary embodiment illustrated in FIG. 6, the backboard 100 is fabricated of a rigid material, such as PVC plastic or fiberglass, with opposed slots 102A, 102B and 104A, 104B at the sides of the board designed to allow movement of the cuffs to accommodate different size patients. The cuffs are threaded through the slots so that when the patient is positioned on the board, the cuffs are easily fastened using hook and loop fasteners.

Figure 7A:
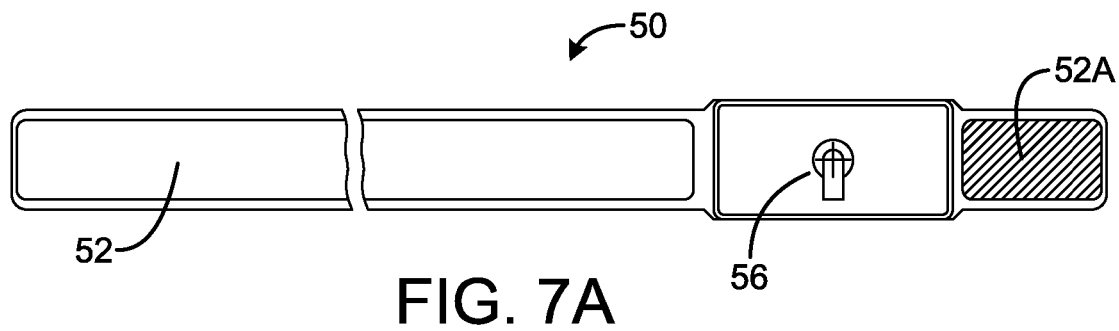
FIGS. 7A-7B illustrate top and bottom views of an exemplary embodiment of the chest cuff for the system of FIG. 1.
Figure 7B:
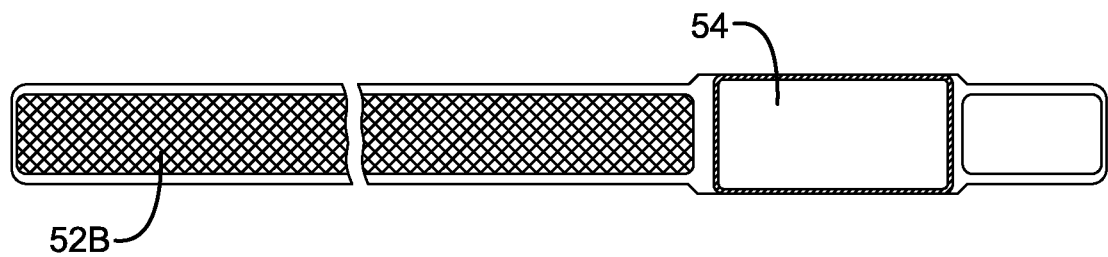
Figure 11:
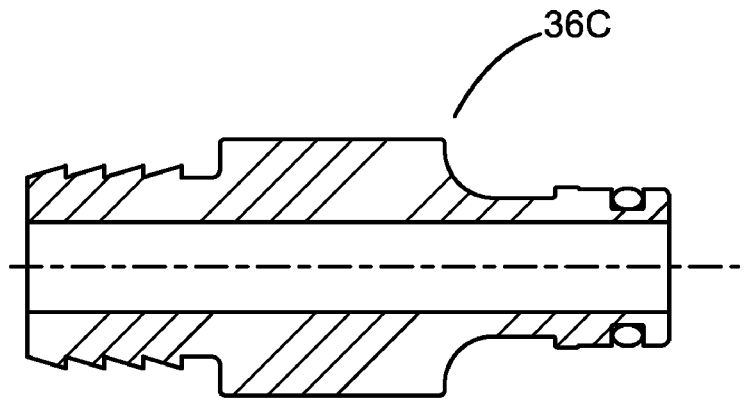
FIG. 11 illustrates one exemplary embodiment of a port connector for the system unit of FIG. 1.
Figure 12:
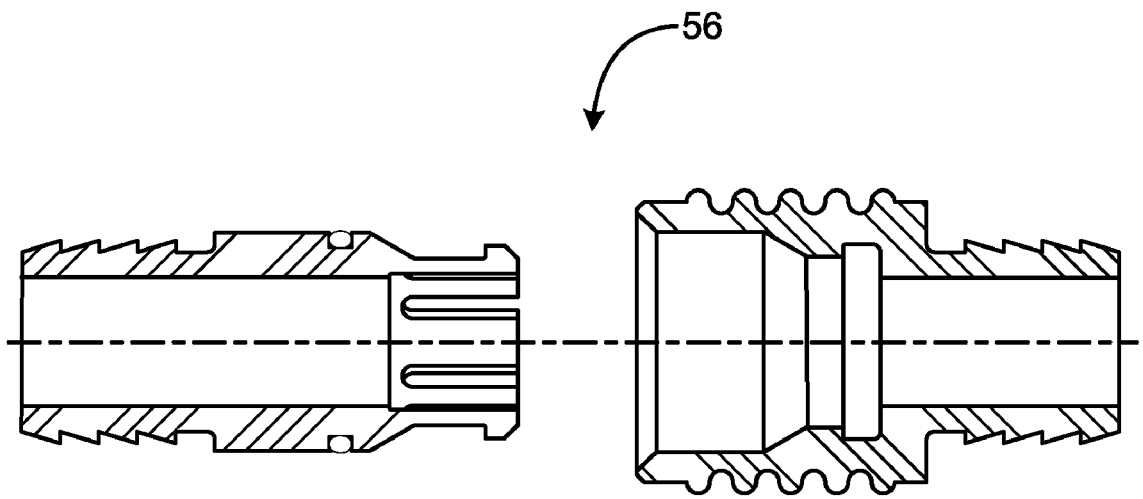
FIG. 12 illustrates an exemplary embodiment of a connector set for connecting an air hose to an inflatable cuff.

FIGS. 7A-7B illustrate an exemplary embodiment of the chest cuff 50. The cuff 50 includes an elongated flexible strap 52, which has affixed at a top surface of one end a hook fastener portion 52A. In an exemplary embodiment, the hook fastener portion is sewn to the top of the strap, as shown in FIG. 7A, and has a sufficient size to withstand the forces applied in use due to inflation of the bladder 54. In one embodiment, the hook fastener portion is 4 inches wide by 7 inches long. On the underside of the strap, and at the opposite strap end from the hook fastener portion, a loop fastener portion 52B is attached to the strap, e.g. by sewing or by adhesive. The loop fastener portion is considerably longer than the hook fastener portion to allow the strap to be fitted to patients of varying sizes and fastened in place. The bladder 54 may be fabricated of a flexible material such as polyurethane, and has a port connector 56 which may be connected to a corresponding connector attached to hose 58 (FIG. 1). In an exemplary embodiment, the connector between the hose and the controller is a color coded, sliding sleeve type as shown in FIG. 11, and the connectors 56 between the hoses and the cuffs are color coded, snap connected units as shown in FIG. 12. The connectors between the hoses and cuffs are designed to be permanent, with no provision for disconnecting. Alternatively the hose may be permanently attached to the bladder port. The opposite end of hose 58 is configured for connection to a port on the unit 30. The bladder may be filled with pressurized air to inflate and apply pressure to the chest of the patient in an exhaling portion of a respiratory cycle, and deflated to allow air into the lungs of the patient, under control of the timer unit and operation of pneumatic solenoid valve 140-2 (FIG. 4A), as described above. The bladders may be of different sizes for different size cuffs, dependant on patient size.

Figure 8A:
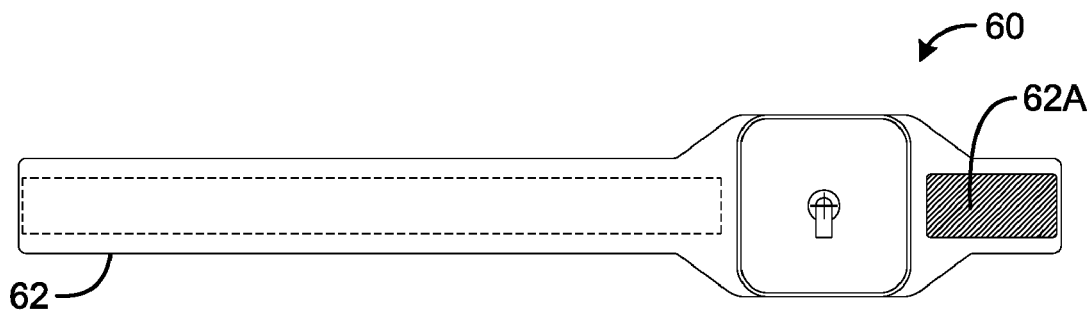
FIGS. 8A-8B are respective top and bottom views of an exemplary embodiment of the abdomen cuff for the system of FIG. 1.
Figure 8B:
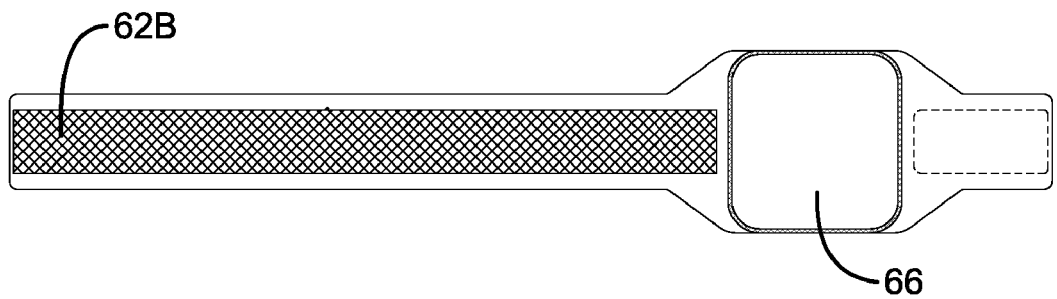

FIGS. 8A and 8B illustrate the abdomen cuff 60, which includes a flexible strip portion 62, with a corresponding hook fastener portion 62A and loop fastener portion 62B attached at opposite ends and on opposite sides of the strap portion. The bladder 64 has a connector 66 for attachment to hose 68. Alternatively, as described above regarding the chest cuff, the hose may be permanently attached to the bladder port. The bladder 64 may be inflated and deflated by operation of the pneumatic solenoid valve 140-3 (FIG. 4A).

Figure 9:
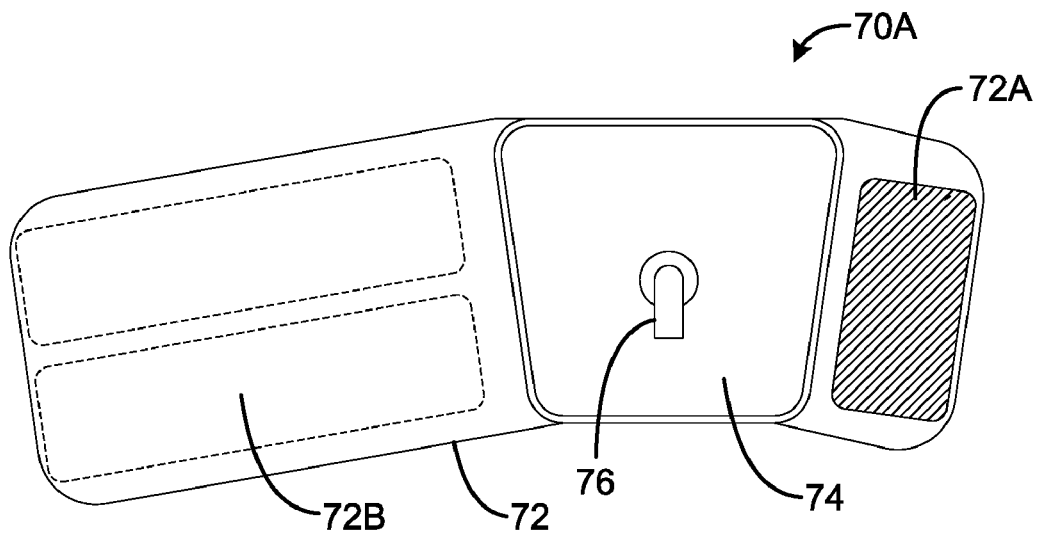
FIG. 9 is a top view of an exemplary embodiment of a leg cuff for the system of FIG. 1.

FIG. 9 illustrates an exemplary leg cuff 70A, which may be used for the right leg or the left leg of the patient. The cuff includes a flexible strap portion 72, with a corresponding hook fastener portion 72A and loop fastener portion 72B attached at opposite ends and on opposite sides of the strap portion. The bladder 74 has a connector 76 for attachment to hose 78 (FIG. 1). Alternatively, as described above regarding the chest cuff, the hose may be permanently attached to the bladder port. The bladder 74 may be inflated and deflated by operation of the pneumatic solenoid valve 140-4 (FIG. 4A). The system preferably includes a leg cuff for each leg, and the bladder connectors joined together by a Y-hose to inflate/deflate the respective leg cuff bladders in unison.

The hoses may be manually attached to the respective cuff bladders by connectors that are designed to make a permanent connection. The cuffs are intended to be a single use only so as to assure sanitation and eliminate any fatigue failures. The connectors on the control unit 30 engage the hoses with a sliding sleeve disconnect for easy connection and disconnection.

In an exemplary embodiment, the patient disposable cuffs comprise a disposable patient kit which may be separately marketed or produced, while being compatible with attachment to the system unit 30. In this regard, each cuff hose will have a connector which is distinguished from the other connectors for the other cuff hoses. This may be a visual feature, e.g. color coding with connectors on the system unit 30, or the connectors may be designed so that the leg cuff hose can only be connected to the proper hose connector on the system unit, for example, or both. The kit may also include a mask with ventilator valve and hose, with the ventilator hose connector further being selected so that it may not physically attached to any of the cuff connectors on the control unit 30.

Figure 10:
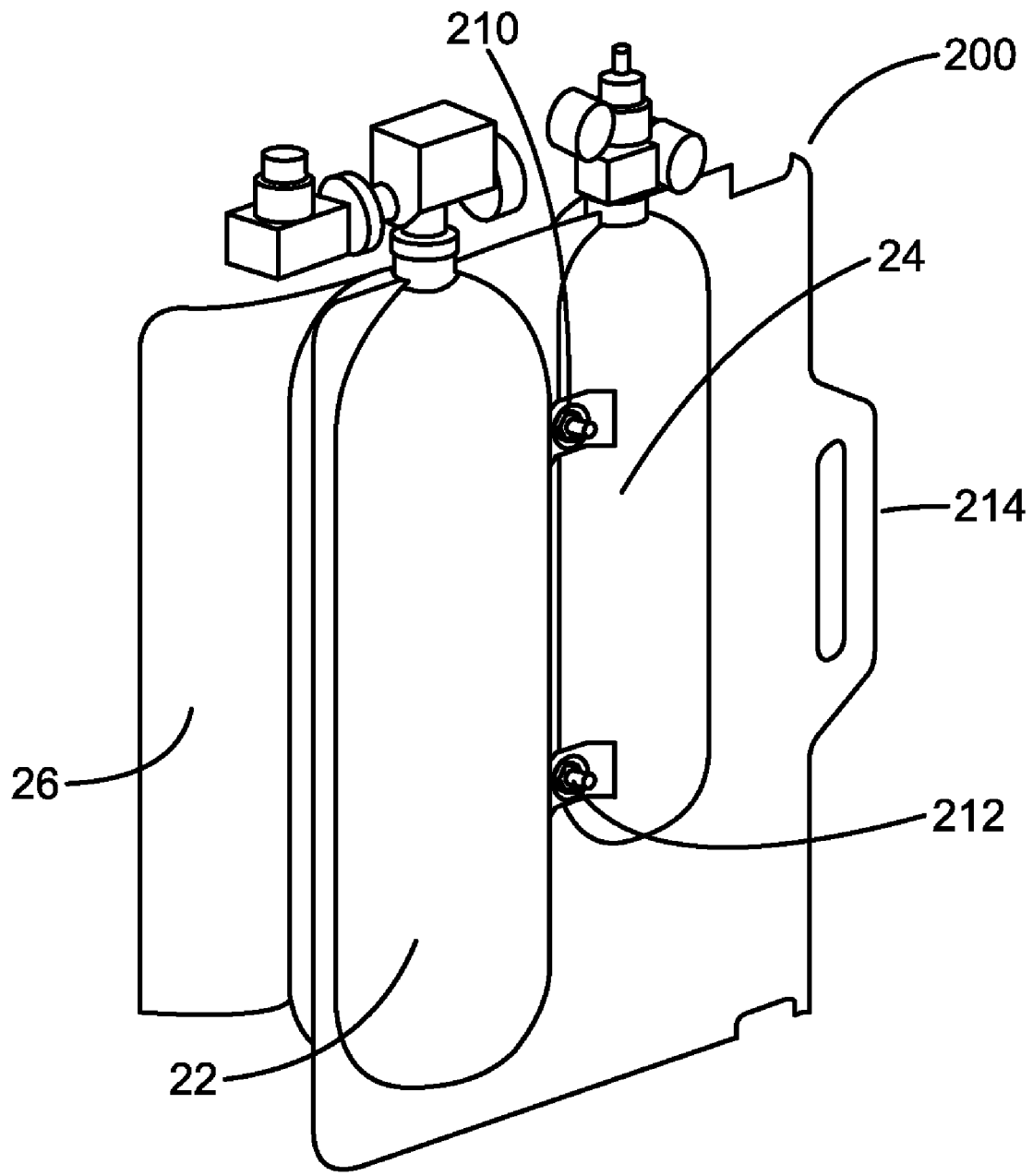
FIG. 10 is a perspective view illustrating a carrier for the gas cylinders of the system of FIG. 1.

FIG. 10 illustrates a tank transport and storage unit 200 designed to allow easy transport of the air and oxygen tanks 22, 24. The tanks fit into cavities formed in the caddy and are retained by bolts 210 and plastic clips 212. The clips are such that by turning them 90 degrees the tanks are released for easy replacement. The hoses are wrapped around the caddy and a hand hold 214 is situated on the side for easy carrying. A detachable back pack 216 allows the tanks to be carried on the back, thus freeing hands for other items.

While the system has been described in the context of a portable resuscitation/respiration system, the system unit 30 may be employed in a stationary or even a built-in application, e.g. in a hospital setting such as an emergency room or critical care unit. The pressurized gases may be supplied by lines from pressurized air and oxygen sources. The system unit can be mounted on a cart, or even built into a wall, and supplied with power by permanent connection. It is anticipated that the patient kit will be for one-time use, for sanitary reasons, and connected to the system unit in the same manner, i.e. by connectors/hoses.

One application for the system illustrated in FIG. 1 is to perform resuscitation on a patient. An exemplary procedure for operating the system in a resuscitation mode may employ two persons, preferably trained in CPR. Before use the control unit 30 may be pre-set to the following positions: Oxygen tidal volume selector to one position of 400, 600, 800 or 1000 ml. The chest cuff valve and the abdomen cuff valve are set to AUTO. The leg cuff valve is set to Off.

1. After determining the condition of the patient, sit the patient upright.
2. Place the backboard with the attached chest and abdomen compression cuffs behind the patient.
3. Lay patient onto the back board.
4. Alternately, place the backboard and cuffs to the patient's side and roll the patient onto the backboard.
5. First attendant: a. apply chest cuff around patient and secure fasteners, b. apply abdomen cuff around patient and secure fasteners, c. connect color coded air supply hoses to cuffs, d. apply leg cuffs and connect color coded air supply hoses, e. turn controller valve for leg cuffs to Auto.
6. Second attendant: a. connect and turn ON air and oxygen supply to controller, b. connect air supply hoses to controller, c. connect oxygen ventilation hose to controller, d. press ON/OFF button—green indicator lights and chest, abdomen and leg cuffs cycle, e. apply oxygen ventilator mask to patient.

Upon successful resuscitation: a. turn tidal volume selector to the Demand position or apply oxygen continuous flow mask to patient, b. turn controller valve for chest cuff to OFF, c. continue to cycle abdomen and leg cuffs to provide circulation support Thus, if the patient returns to spontaneous breathing, the tidal volume selector can be set to the "demand" mode. In this mode, the ventilator is disconnected from automatic ventilation and provides oxygen ventilation with each breath of the patient.

If the patient returns to cardiac arrest: a. reset tidal volume selector to previous setting, b. turn controller valve for chest cuff to ON, and automatic cardiopulmonary resuscitation resumes.

Upon completion of resuscitation procedure: press the ON/OFF button—green indicator turns off and automatic oxygen ventilation and cuff cycles cease, disconnect the color coded air supply hoses from controller and cuffs, disconnect the oxygen ventilator hose from the control unit, disconnect the air and oxygen supply hoses from the control unit, open the cuff fasteners and remove from the patient.

Exemplary embodiments of the resuscitation/respiration system can be used in several applications or operating modes, and may thus perform the functions of one of more of the following applications.

1. Cardiopulmonary resuscitation, as described above.
2. Circulation support mode. After resuscitation a weakened heart may produce low cardiac output which results in inadequate blood pressure and reduced blood flow to the brain, heart, kidneys and lungs. The circulation support feature helps reduce stress on the weakened heart during transportation to the hospital. In this mode: a. turn tidal volume selector to Demand position or apply oxygen continuous flow mask to patient, b. turn controller valve for chest cuff to OFF, c. continue to cycle abdomen and leg cuffs to provide circulation support.
3. Transport ventilation. Patients in respiratory arrest or respiratory stress may require ventilation, where the ability to breathe is absent or impaired. In a transport ventilation mode, the system can act as a transport ventilator, and its selectable oxygen volume provide artificial oxygen ventilation of the lungs at a frequency of 15 breaths per minute. In this case the patient would need only respiratory support and would be fitted with a mask and connected to the ventilator. If the patient were breathing spontaneously the tidal volume selector would be set in the "demand" mode, if not it would be set to the appropriate tidal volume setting. The valves 36B, 36C and 36D would be set to the OFF position.
4. Anti-Shock system. Medical anti-shock trousers (MAST) have been used to increase venous return to the heart during traumatic and hemorrhagic shock until definitive care could be given. This, combined with compression of blood vessels, causes the movement of blood from the lower body to the brain, heart and lungs. The cycling action of the leg and abdomen cuffs may be used to restore blood pressure and return heart rate to normal. For anti-shock applications, the system would be set for legs only inflation, with valve 36D in the "ON" position and valves 36B and 36C in the OFF position. As such it would function similar to anti-shock trousers (MAST). In more severe cases, e.g. for patients in a traumatic and/or hemorrhagic shock condition, the system would be set to cycle the abdomen and legs in "automatic" mode. Unlike conventional medical anti-shock trousers that are statically inflated to force blood from the lower body to the brain, heart and lungs, the abdomen and leg cuffs may be cycled in the usual rhythm described above for the resuscitation mode. Those patients in shock with either no or low blood pressure and rapid heart rate, (a typical shock condition) may have their condition reversed relatively quickly, e.g. in 1-3 minutes.

In accordance with a further embodiment, the system may be employed to facilitate the distribution of medications, by enhancing intraveneous (IV) medication and fluid infusion rates. Cardiac arrest and resultant circulatory shock lead to organ hypoperfusion, circulatory shunting, cellular dysfunction, and ultimately death. Circulatory shock also complicates distribution of medications that are administered during cardiopulmonary resuscitation, such as epinephrine, lidocaine, etc., even when conventional manual CPR protocols are being utilized. Clearly, medications must reach their sites of action in order to increase the likelihood of Return of Spontaneous Circulation (ROSC), but will not as long as circulatory pumping is impaired.

Figure 16:
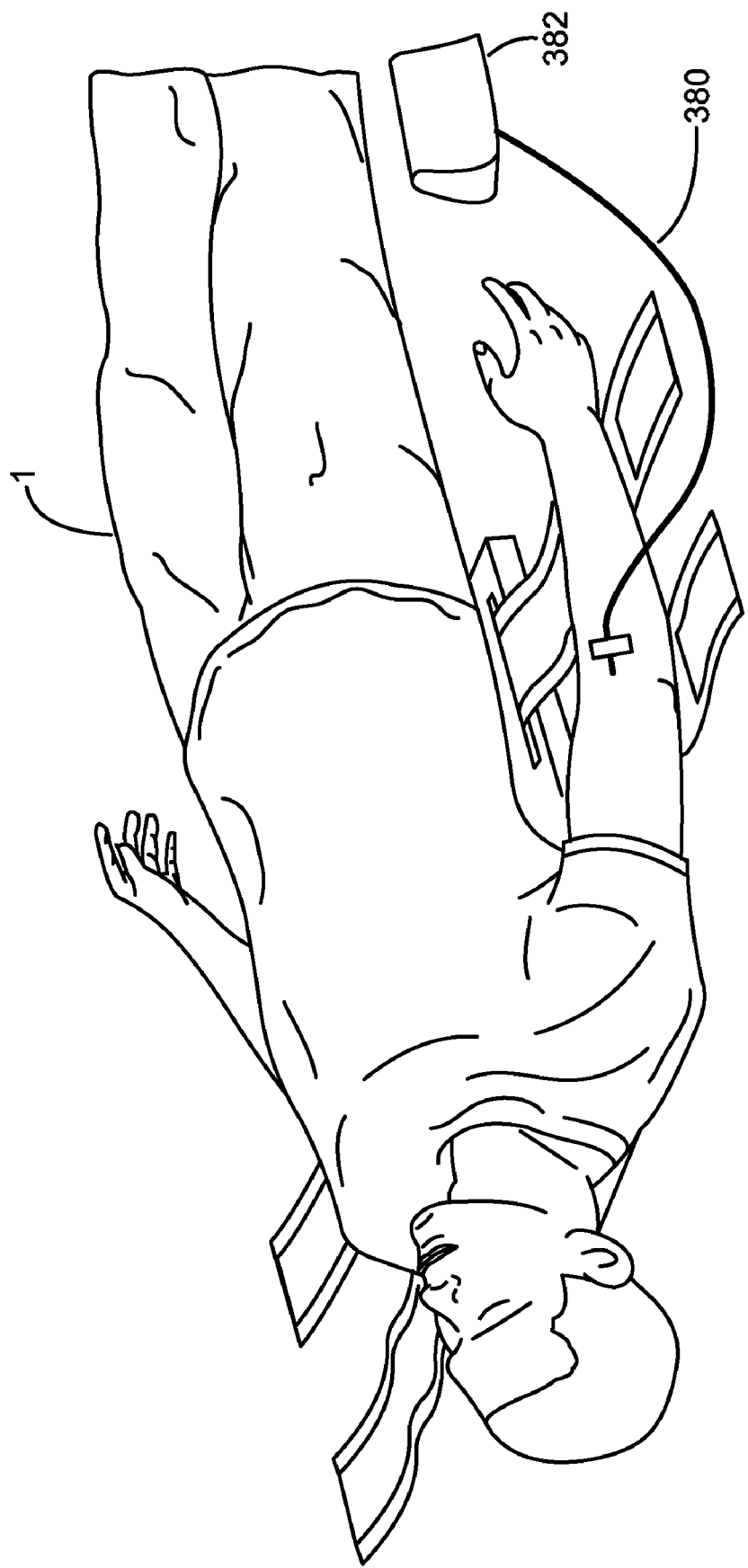
FIG. 16 is a diagrammatic view illustrating a patient arranged on an exemplary embodiment of a backboard as in FIG. 14 with the chest and abdomen cuffs deployed in preparation for attachment to the patient's chest and abdomen, and showing an IV connected to the patient's arm.

In accordance with this aspect, as illustrated in FIGS. 1 and 16, an IV line 380 is intraveneously connected to the patient 1 prior to or during the use of the system 10 with the medication and/or fluid to be administered in an IV bag 382. With the system 10 connected to the patient and in operation, blood flow is greatly augmented by the inflation/deflation cycling of the chest, abdomen, and, if connected, the leg compression cuffs, since there are now multiple external circulatory pumps instead of the single point manual chest compression site over the sternum. This overcomes the vicious cycle of shock, facilitating volume replacement and concomitantly proper distribution of cardio-stimulatory drugs to improve chances of ROSC.

A further embodiment involves the integration of defibrillator pads with the compression cuffs. The American Heart Association (AHA) protocol for patients in cardiac arrest with certain dangerous arrhythmias is to apply defibrillator electrode pads to the patient chest, followed by rhythm analysis and up to a series of three shocks, followed by cardiopulmonary resuscitation for one minute. After one minute, interrupt CPR, apply three more shocks to the patient and resume CPR. AHA guidelines advise that "patient chest hair may prevent effective electrode pad contact with the skin causing high transthoracic impendence resulting in ineffective defibrillator shock." If the defibrillator produces a message to check electrodes or check electrode pads the problem may be resolved by pressing firmly on the pads," according to AHA guidelines.

Figure 13:
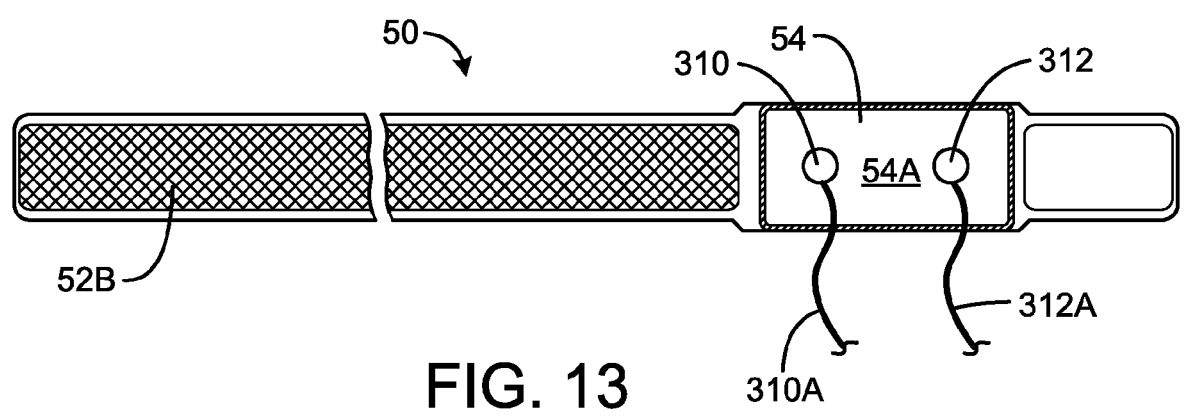
FIG. 13 illustrates an exemplary embodiment of a chest cuff having a pair of electrodes attached to the bladder surface facing the patient's chest.

An enhanced patient kit provides the means to preposition defibrillator electrode pads into the compression cuffs thereby reducing the vital time to apply the pads to the patient prior to or during the resuscitation process. The tight circumferential wrapping of the compression cuffs enhance electrode contact with the patient minimizing the possibility of transthoracic impedance. An exemplary embodiment is illustrated in FIG. 13, in which the chest cuff bladder 54 has affixed to the underside surface 54A at least one, and in this example, two electrode pads 310 and 312, each with a respective electrode wire 310A and 312A for connection to a system such as a defibrillator, or other patient monitoring or treatment system such as an EKG. The electrode pads are positioned in a position on the surface 54A selected so that the electrodes will be properly positioned for contact against the patient's chest. The electrode pads may be attached to the chest cuff by adhesive or other attachment methods, such as by adhesive, rf welding or ultrasonic welding. The patient's clothing will typically be removed to allow direct contact of the electrodes with the patient's skin.

To further facilitate rapid and proper positioning of the patient kit elements on the patient, the backboard or patient platform may be provided with a patient positioning system. The anatomical symbol for man, (shown as element 318) in FIG. 14) is located at the top of the patient platform. After the patient is placed into the sitting position, the backboard 100 is positioned behind the patient. The anatomical symbol 318 serves as an orientation guideline when applying the backboard 100 and the chest and abdomen cuffs to the patient.

Abdomen and chest compression cuffs are threaded into the patient backboard 100 in a ready, prepositioned position for application to the patient. Prepositioned cuffs on the platform facilitate alignment with patient abdomen and chest thereby reducing CPR initiation time.

To further facilitate the rapid attachment of the compression cuffs to the patient, a cuff prepositioning system, in an exemplary embodiment a cuff lanyard system 320 (FIGS. 14, 14A and 15), may be employed to secure the chest and abdomen compression cuffs 50 and 60 to the patient platform 100 in a storage or ready position and facilitate rapid deployment of the cuffs for use on the patient. In an exemplary embodiment, the ends of abdomen and chest compression cuffs 50 and 60 are folded in an accordion-like fashion and the folded end portions 50A, 50B and 60A, 60B are secured on either side of the patient platform by the cuff prepositioning system, in this embodiment the retaining strap portions 330 and 340 of the lanyard system 320. The retaining straps are wrapped around each folded cuff flap portion and are secured by hook and loop fasteners sewn to the straps. The two straps are joined together with a pull ring 322 to form the lanyard system 320. Alternatively, the lanyard system could be formed of a single strap, folded and secured at its midpoint to the ring 322. After the patient is set upward and the platform 100 positioned behind him, the medical attendant on the right side of the patient pulls the lanyard away from the platform and the folded cuff flaps fold away from the platform in opposing directions. The patient is laid back on the exposed platform and the opposing cuff flaps are enclosed around the patient and fastened with their hook and loop fasteners.

In an alternate embodiment, the cuff prepositioning system may be an elastic or tearable member such as an elastic cord or a tearable wrapper arranged to release upon manual manipulation by an attendant, allowing individual manual deployment of each folded cuff portion.

Inflation compression cuffs 50 and 60 for application to a patient in a state of circulatory impairment such as cardiac arrest, shock or similar condition are attached to a patient platform to facilitate rapid application. As described above with respect to FIGS. 7A-9, for example, the chest and abdomen compression cuffs 50 and 60 have inflatable bladders, and end portions that are folded and secured on either side of the patient platform by retaining straps. One end or portion 330 of the retaining strap or lanyard system 320 wraps around the folded chest compression cuff portions and the opposite end portion 340 of the lanyard system wraps around the folded abdomen compression cuff portions. The two strap portions join together with the pull ring 322 to form the lanyard that when rapidly pulled in a right angle away from the patient platform causes the folded chest and abdomen cuff portions to unfold in opposing directions from the platform 100, thereby exposing the platform for patient positioning and rapid application of cuffs around the patient chest and abdomen.

Figure 15:
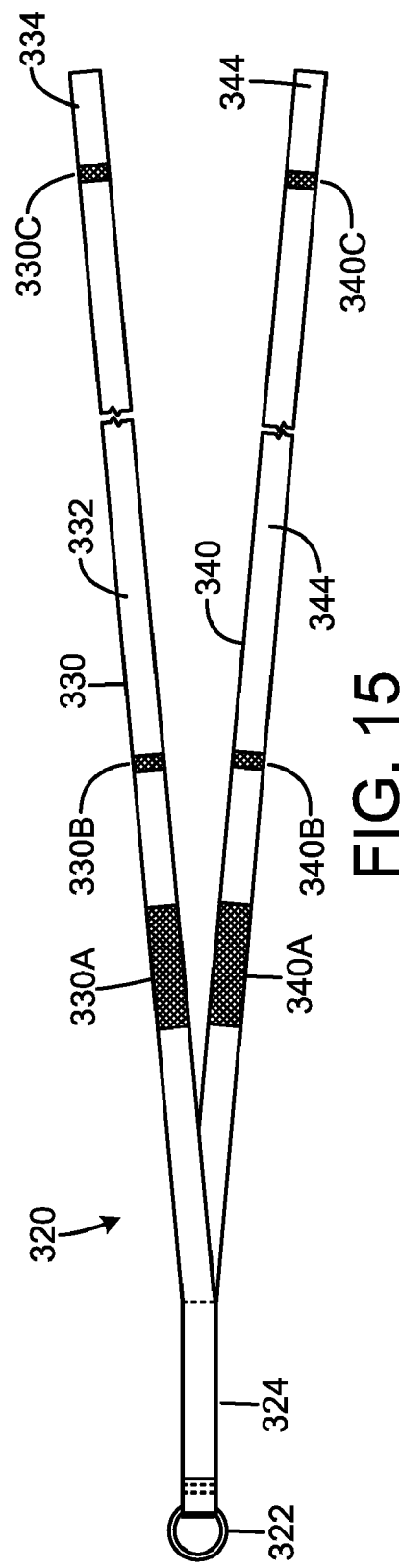
FIG. 15 is a diagrammatic top view illustrating an exemplary embodiment of a lanyard configuration suitable for use with the patient backboard system illustrated in FIG. 14.
Figure 15A:
FIG. 15A illustrated the underside surface of a distal end of retaining strap portions of the lanyard configuration.

The lanyard system 320 is illustrated in further detail in FIGS. 15 and 15A. Retaining strap portion 330 has one end attached to the ring 322, and hook fastener portion 330C formed on its upper or first surface 332 adjacent its terminal end 334. The strap portion 330 also has a hook fastener portion 330A and a loop fastener portion 330B formed on the surface 332 in spaced relation. Similarly, the retaining strap portion 340 has one end attached to the ring 322, and hook fastener portion 340C formed on its upper or first surface 342 adjacent its terminal end 344. The strap portion 340 also has hook fastener portion 340A and loop fastener 340B formed on the surface 342 in spaced relation. Both strap portions have a loop fastener portion 330D, 340D on the under side or second surface 336, 346 adjacent the respective terminal end.

Figure 14:
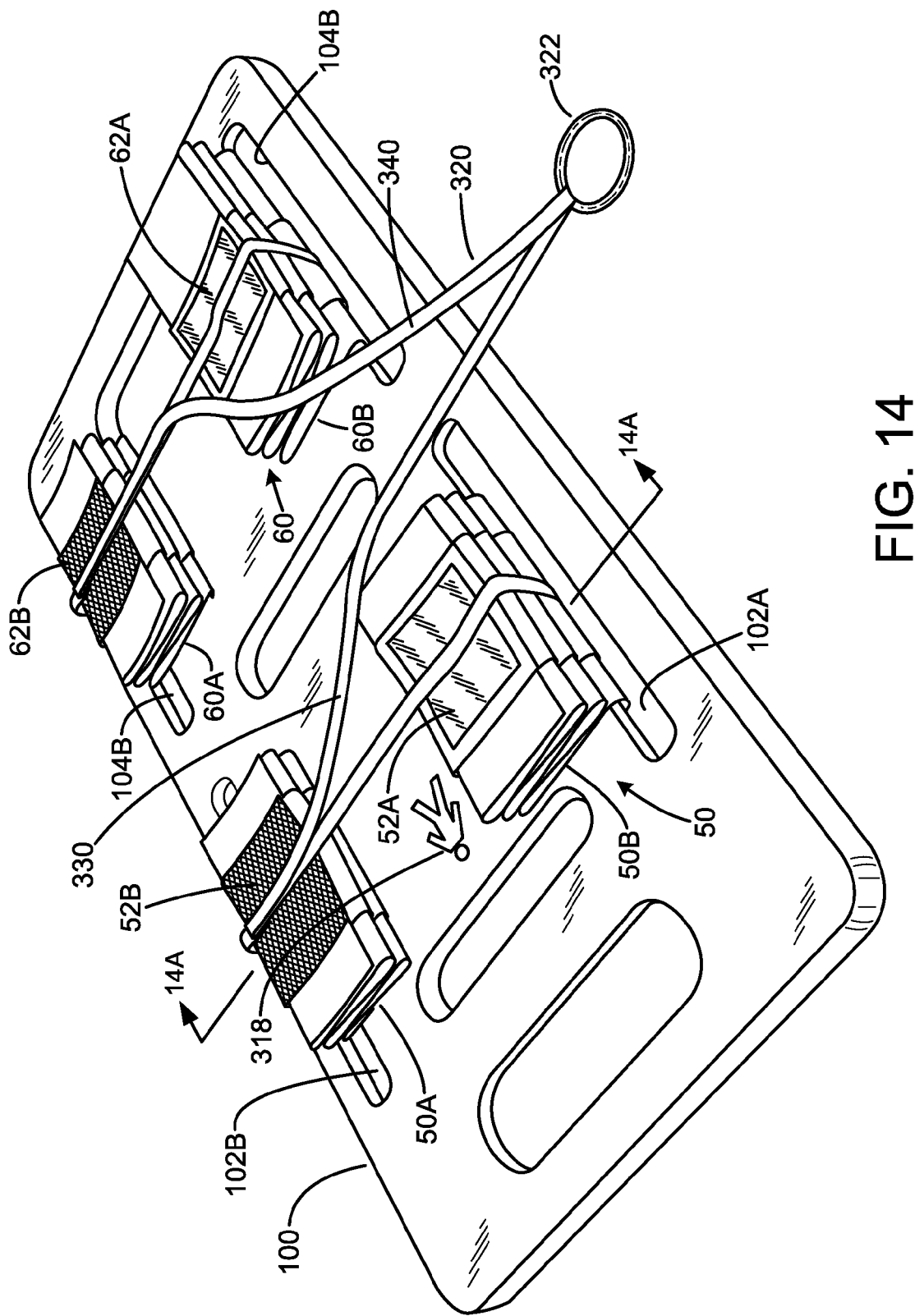
FIG. 14 illustrates an exemplary embodiment of a patient backboard or platform having the chest and abdomen cuffs secured in a ready configuration by a lanyard system.
Figure 14A:
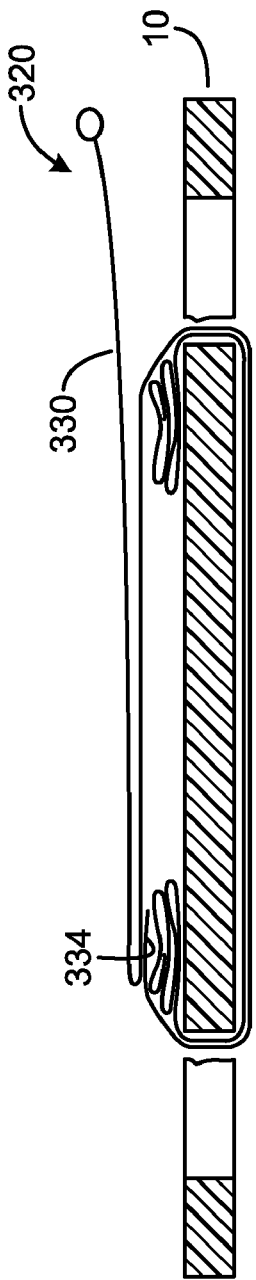
FIG. 14A is a diagrammatic cutaway view along line 14A-14A of FIG. 14, illustrating an exemplary lanyard rigging embodiment to secure the cuffs in the ready position.

FIGS. 14 and 14A illustrates an exemplary rigging configuration for securing the chest and abdomen cuffs to the patient platform 100 using the lanyard system 320. Only the chest cuff 50 and lanyard strap 330 are shown in FIG. 14A, although the rigging of the abdomen cuff with strap 340 may be identical. The chest cuff 50 has its midsection under the platform, with the opposed ends passed through the slots 102A, 102B of the platform and brought up through the slots. The opposing end portions are folded accordion-style, to form the folded chest cuff portions 50A, 50B. In this folded position, the hook fastener portion 52A and loop fastener portion 52B are exposed on top of the respective folded cuff portions. In a similar fashion, the abdomen cuff 60 has its midsection under the platform, with the opposed ends passed through the slots 104A, 104B of the platform and brought up through the slots. The opposing end portions are folded accordion-style, to form the folded chest cuff portions 60A, 60B. In this folded position, the hook fastener portion 62A and loop fastener portion 62B are exposed on top of the respective folded cuff portions. The strap portion 330 is wrapped around the patient platform, with the terminal end 334 passed through slot 102A, under the patient platform, and up through the slot 104B or over the side of the patient platform. The hook fastener portion 330C on the terminal end of the retaining strap portion 330 attaches to the loop fastener portion 52B of chest cuff 50. The portion of the strap portion 330 on the top of the platform is folded over onto itself at the chest cuff portion 50A. The strap portion is tightened, and loop fastener portion 330B of the strap portion 330 attaches to hook fastener portion 52A of the chest cuff 50. The hook fastener portion 330A on the surface 334 of the distal end 334 of the strap portion 330 attaches to the retaining strap loop fastener portion 330D, on the underside 336 of retaining strap 330.

In a similar fashion, retaining strap portion 340 is wrapped around the patient platform and hook fastener portion 340C on the terminal end 344 attaches to loop fastener portion 62B of abdomen cuff 60. The portion of the strap portion 340 on the top of the platform is folded over onto itself at the chest cuff portion 60A. The strap portion is tightened, and loop fastener portion 340B of the strap portion 340 attaches to hook fastener portion 62A of the abdomen cuff 60. The hook fastener portion 340A on the surface 342 of the distal end 344 of the strap portion 340 attaches to the retaining strap loop fastener portion 340D, on the underside 346 of retaining strap 340.

The retaining strap portions 330 and 340 join together at pull strap portion 324 and pull ring 322 to form the cuff lanyard assembly.

In accordance with an exemplary embodiment, the patient in a state of circulatory impairment such as cardiac arrest, shock or similar condition is positioned forward in a folding like motion by medical attendants. The patient platform 100, with chest and abdomen cuffs 50 and 60 retained in place by the lanyard system 320, is placed longitudinally behind the patient in accordance with the platform's anatomical symbol 318 of a human. The medical attendant to the right of the patient grasps the lanyard pull ring and rapidly pulls at a right angle away from the patient platform. The rapid pull of the lanyard causes hook fasteners 330A and 340A of retaining strap portions 330 and 340 to detach from the loop fasteners 330D and 340D of the respective strap portions 330 and 340. As the lanyard is pulled away from the platform, loop fasteners 330B and 340D attached to the folded portions 50B and 60B of the chest cuff and abdomen cuff pull on the folded portions 50B, 60B, causing these portions to unfold in the same direction from the platform as the ring is being pulled. As the medical attendant completes the right angle pull on the lanyard system, now the lanyard portion under the platform is pulled, exerting a pull force on the distal ends 334, 344, and the hook fastener portions 330C, 340C attached to the folded chest cuff portions 50A and 60A of the chest cuff and abdomen cuff pull in the direction opposed to the lanyard ring pull, causing the cuff portions 50A, 60A to unfold in an opposite direction from the platform. With the cuff assemblies unfolded away from the platform, the patient is laid back upon the platform and each cuff is secured around the patient with its hook and loop fasteners. Rapid deployment is complete and the medical procedure commences.

Although the foregoing has been a description and illustration of specific embodiments of the subject matter, various modifications and changes thereto can be made by persons skilled in the art without departing from the scope and spirit of the invention.

What is claimed is:

1. A patient interface kit for a system for providing cardiopulmonary resuscitation or circulatory support to a patient, the system including a control unit, the kit comprising:
   an inflatable abdominal cuff adapted to extend over a patient's abdomen and including an elongated flexible strap, an inflatable bladder and a fastener system to secure the abdominal cuff in position for use on a patient;
   an inflatable chest cuff adapted to extend over a patient's chest and including an elongated flexible strap, an inflatable bladder and a fastener system to secure the chest cuff in position for use on a patient;
   a patient platform or backboard configured for disposition against the patient's back during use; and
   a cuff prepositioning system configured to secure the chest and abdomen compression cuffs to the patient platform in a ready position and to facilitate rapid deployment of the cuffs for use on the patient, wherein ends of abdomen and chest compression cuffs are folded in an accordion fashion to form folded end portions secured on either longitudinal side of the patient platform by the cuff prepositioning system, ready for deployment outwardly away from the platform to be attached to the patient, and the cuff prepositioning system is arranged to releasably secure the folded end portions in the ready position on the patient platform.

2. The kit of claim 1, wherein the patient backboard is fabricated of a rigid material.

3. The kit of claim 1, wherein the patient backboard has a top and a bottom, and includes a visual patient positioning indicator.

4. The kit of claim 3, wherein the patient positioning indicator comprises a symbol located on the patient platform in a position indicating proper orientation of the platform relative to the patient for use.

5. The kit of claim 1, wherein the cuff prepositioning system includes opposed slots at longitudinal sides of the patient platform configured to receive ends of the straps of the respective chest and abdomen cuffs there through, and wherein intermediate portions of the respective chest and abdomen cuffs are positioned under the patient platform, and ends of the respective cuffs are threaded through the slots.

6. The kit of claim 1, further comprising:
   at least a first electrode attached to a surface of the chest cuff and positioned to be adjacent the patient's heart with the cuff secured in position on the patient's chest, and a first wiring lead configured for attachment to a utilization device.

7. The kit of claim 5, wherein the cuff prepositioning system includes a lanyard system, comprising a first strap portion arranged to secure respective first and second folded end portions of the chest cuff in the ready position to the patient platform, and a second strap portion arranged to secure respective first and second folded end portions of the chest cuff in the ready position to the patient platform.

8. The kit of claim 7, wherein a first portion of the first strap portion is passed under the patient platform and a terminal end is releasably connected to the first folded end portion of the chest cuff, an intermediate portion is folded over onto itself and attached to the second folded end portion of the chest cuff, and a lanyard strap portion available to an attendant, such that pulling the lanyard strap portion in a direction transverse to a longitudinal axis of the patient platform deploys the first and second folded end portions in opposed directions outwardly from the patient platform.

9. The kit of claim 8, wherein a first portion of the second strap portion is passed under the patient platform and a terminal end is releasably connected to the first folded end portion of the abdominal cuff, an intermediate portion is folded over onto itself and attached to the second folded end portion of the abdominal cuff, and a lanyard strap portion available to an attendant, such that pulling the lanyard strap portion in a direction transverse to a longitudinal axis of the patient platform deploys the first and second folded end portions in opposed directions outwardly from the patient platform.

10. The kit of claim 9, wherein the lanyard strap portions of the first and second strap portions are joined together.

11. The kit of claim 9, wherein each of said cuffs include hook and loop fasteners to secure the cuffs in position for use on a patient, and wherein the hook and loop fasteners of each cuff are engaged by corresponding loop and hook fasteners on the cuff prepositioning system to releasably secure the cuffs in a ready position.

12. The kit of claim 1, further comprising:
at least one leg cuff adapted to extend around a patient's leg and including an flexible strap, an inflatable bladder and a fastener system to secure the leg cuff in position for use on the patient.

13. The kit of claim 12, further comprising a face mask with a ventilator valve.

14. A patient interface kit for a system for providing cardiopulmonary resuscitation or circulatory support to a patient, the system including a control unit, the kit comprising:
an inflatable abdominal cuff adapted to extend over a patient's abdomen and including an elongated flexible strap, an inflatable bladder and a fastener system to secure the abdominal cuff in position for use on a patient;
an inflatable chest cuff adapted to extend over a patient's chest and including an elongated flexible strap, an inflatable bladder and a fastener system to secure the chest cuff in position for use on a patient;
a patient platform or backboard configured for disposition against the patient's back during use;
the patient platform or backboard including a visual patient positioning indicator;
a cuff prepositioning system configured to secure the chest and abdomen compression cuffs to the patient platform in a ready position and to facilitate rapid deployment of the cuffs for use on the patient;
the cuff prepositioning system including opposed slots at longitudinal sides of the patient platform configured to receive ends of the straps of the respective chest and abdomen cuffs there through, and wherein intermediate portions of the respective chest and abdomen cuffs are positioned under the patient platform, and ends of the respective cuffs are threaded through the slots; and
wherein the ends of abdomen and chest compression cuffs are folded in an accordion fashion to form folded end portions secured on either longitudinal side of the patient platform by the cuff prepositioning system, ready for deployment outwardly away from the platform to be attached to the patient, and the cuff prepositioning system is arranged to releasably secure the folded end portions in the ready position on the patient platform.

15. The kit of claim 14, wherein the cuff prepositioning system includes a lanyard system, comprising a first strap portion arranged to secure respective first and second folded end portions of the chest cuff in the ready position to the patient platform, and a second strap portion arranged to secure respective first and second folded end portions of the chest cuff in the ready position to the patient platform.

16. The kit of claim 15, wherein a first portion of the first strap portion is passed under the patient platform and a terminal end is releasably connected to the first folded end portion of the chest cuff, an intermediate portion is folded over onto itself and attached to the second folded end portion of the chest cuff, and a lanyard strap portion available to an attendant, such that pulling the lanyard strap portion in a direction transverse to a longitudinal axis of the patient platform deploys the first and second folded end portions in opposed directions outwardly from the patient platform.

17. The kit of claim 16, wherein a first portion of the second strap portion is passed under the patient platform and a terminal end is releasably connected to the first folded end portion of the abdominal cuff, an intermediate portion is folded over onto itself and attached to the second folded end portion of the abdominal cuff, and a lanyard strap portion available to an attendant, such that pulling the lanyard strap portion in a direction transverse to a longitudinal axis of the patient platform deploys the first and second folded end portions in opposed directions outwardly from the patient platform.

18. The kit of claim 17, wherein the lanyard strap portions of the first and second strap portions are joined together.

19. The kit of claim 17, wherein each of said cuffs include hook and loop fasteners to secure the cuffs in position for use on a patient, and wherein the hook and loop fasteners of each cuff are engaged by corresponding loop and hook fasteners on the cuff prepositioning system to releasably secure the cuffs in a ready position.

20. The kit of claim 14, further comprising:
at least a first electrode attached to a surface of the chest cuff and positioned to be adjacent the patient's heart with the cuff secured in position on the patient's chest, and a first wiring lead configured for attachment to a utilization device.

21. The kit of claim 14, further comprising:
at least one leg cuff adapted to extend around a patient's leg and including an flexible strap, an inflatable bladder and a fastener system to secure the leg cuff in position for use on the patient.

22. The kit of claim 21, further comprising a face mask with a ventilator valve.

* * * * *